United States Patent
Olbricht et al.

(10) Patent No.: US 9,844,585 B2
(45) Date of Patent: Dec. 19, 2017

(54) CONVECTION ENHANCED DELIVERY APPARATUS, METHOD, AND APPLICATION

(71) Applicants: William L. Olbricht, Ithaca, NY (US); Keith B. Neeves, Philadelphia, PA (US); Conor Foley, Ithaca, NY (US); Russell T. Matthews, Skaneateles, NY (US); W. Mark Saltzman, New Haven, CT (US); Andrew Sawyer, New Haven, CT (US)

(72) Inventors: William L. Olbricht, Ithaca, NY (US); Keith B. Neeves, Philadelphia, PA (US); Conor Foley, Ithaca, NY (US); Russell T. Matthews, Skaneateles, NY (US); W. Mark Saltzman, New Haven, CT (US); Andrew Sawyer, New Haven, CT (US)

(73) Assignees: YALE UNIVERSITY, New Haven, CT (US); CORNELL UNIVERSITY, Ithaca, NY (US)

(*) Notice: Subject to any disclaimer, the term of this patent is extended or adjusted under 35 U.S.C. 154(b) by 88 days.

(21) Appl. No.: 14/314,119

(22) Filed: Jun. 25, 2014

(65) Prior Publication Data
US 2014/0371712 A1  Dec. 18, 2014

Related U.S. Application Data

(63) Continuation of application No. 12/525,393, filed as application No. PCT/US2008/053716 on Feb. 12, 2008, now Pat. No. 8,790,317.
(Continued)

(51) Int. Cl.
*A61M 37/00* (2006.01)
*A61K 38/47* (2006.01)
*A61M 5/14* (2006.01)

(52) U.S. Cl.
CPC .......... *A61K 38/47* (2013.01); *A61M 5/1408* (2013.01); *A61M 37/00* (2013.01);
(Continued)

(58) Field of Classification Search
CPC ........ A61M 37/0015; A61M 2037/003; A61M 2037/0046
See application file for complete search history.

(56) References Cited

U.S. PATENT DOCUMENTS

| 6,193,963 B1 * | 2/2001 | Stern ...................... C07K 16/40 424/94.6 |
| 2005/0137531 A1 * | 6/2005 | Prausnitz ............. A61B 5/1411 604/173 |

(Continued)

OTHER PUBLICATIONS

Rapoport "Osmotic Opening of the Blood-Brain Barrier: Principles, Mechanism, and Therapeutic Applications", 2000, Cellular and Molecular Neurobiology, vol. 20, No. 2, 217-230.*

*Primary Examiner* — Bradley Osinski
(74) *Attorney, Agent, or Firm* — Bond, Schoeneck & King, PLLC; William Greener

(57) ABSTRACT

An embodiment of the invention is directed to a microfabricated, silicon-based, Convection Enhanced Delivery (CED) device. The device comprises a silicon shank portion, at least one individual parylene channel disposed along at least a part of an entire length of the shank, wherein the channel has one or more dimensioned fluid exit ports disposed at one or more respective locations of the channel and a fluid (drug) input opening. The fluid input opening may be configured or adapted to be connected to a fluid reservoir and/or a pump and/or a meter and/or a valve or other suitable control device(s) or apparatus that supplies and/or delivers fluid (e.g., a drug) to the microfabricated (Continued)

device. The device may have multiple channels disposed side by side or in different surfaces of the device. The device may be rigid, or flexible, in which case a flexible device can be attached to a bio-degradable support scaffold that provides sufficient structural rigidity for insertion of the device into the target tissue. In certain "functionalized" embodiments of the invention, the CED device is equipped with integrated electrodes and/or a sensor (e.g., glutamate) to detect and convey selective parametric information. Another embodiment of the invention is directed to a CED method for drugs and/or other agents. The method may comprise the delivery of enzymes or other materials to modify tissue permeability and improve drug diffusion. Another embodiment of the invention is directed to a method for making a device for CED of drugs.

12 Claims, 22 Drawing Sheets

Related U.S. Application Data

(60) Provisional application No. 60/889,555, filed on Feb. 13, 2007.

(52) U.S. Cl.
CPC ... *A61M 37/0015* (2013.01); *A61M 2037/003* (2013.01); *A61M 2037/0023* (2013.01); *A61M 2210/0693* (2013.01); *C12Y 302/01* (2013.01); *C12Y 302/01035* (2013.01)

(56) References Cited

U.S. PATENT DOCUMENTS

2005/0143790 A1* 6/2005 Kipke ............... A61B 5/04001
607/60
2011/0184503 A1* 7/2011 Xu ..................... A61B 5/04001
607/116

* cited by examiner

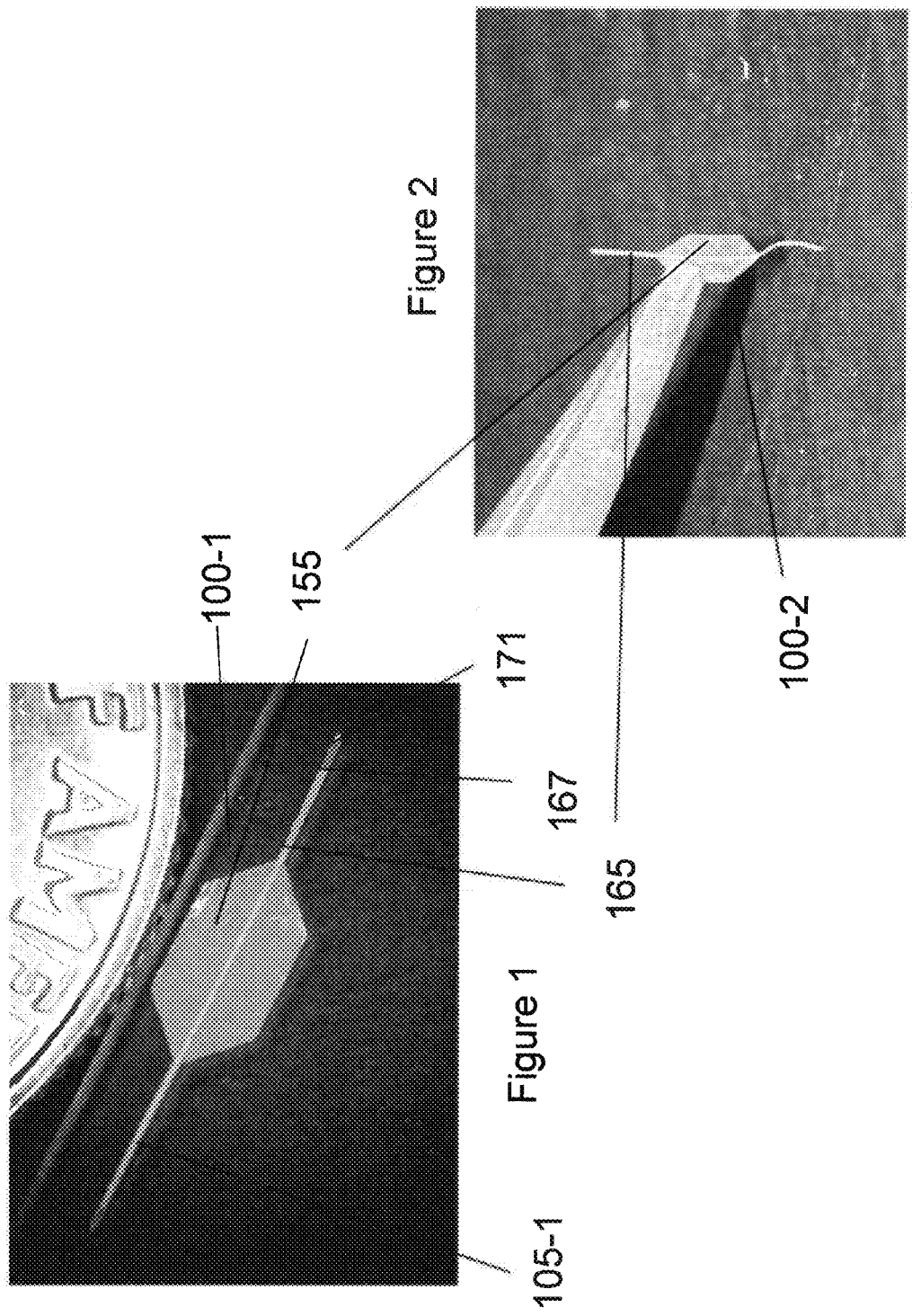

CONVECTION ENHANCED DELIVERY APPARATUS, METHOD, AND APPLICATION

RELATED APPLICATION DATA

The instant application is a CONTINUATION of U.S. application Ser. No. 12/525,393 filed Jul. 31, 2009, which was a US National Stage filing from PCT/US2008/53716 filed 12 Feb. 2008, and claims priority to U.S. provisional application Ser. No. 60/889,555 entitled Convection Enhanced Delivery Apparatus, Method, and Application filed on Feb. 13, 2007 and incorporated herein by reference in its entirety.

FEDERALLY SPONSORED RESEARCH

Certain embodiments and aspects of the disclosed invention were made with government support under Contract No. NS-045236 awarded by the National Institutes of Health. The work reported herein was performed in part at the Cornell NanoScale Facility, a member of the National Nanotechnology Infrastructure Network, which is supported by the National Science Foundation Grant ECS 03-35765. The United States government has certain rights in the invention.

BACKGROUND

1. Field of the Invention

Embodiments of the invention pertain generally to the field of Convection Enhanced Delivery (CED) of therapeutic and/or diagnostic agents (hereinafter referred to as, but not limited per se to, "drugs"). More particularly, embodiments of the invention pertain to microfabricated, microfluidic CED devices, manufacturing methods, and methods for the convection enhanced delivery of a drug.

2. Description of Related Art

Numerous localized drug delivery strategies have been developed to circumvent the blood brain barrier. For example, the insertion of polymeric implants that release drugs slowly into the surrounding tissue has been reported to be successful in treating tissues locally. These implants also can be effective in treating intracranial tumors with local chemotherapy because high drug doses can be delivered to the tissue surrounding the implant. However, it is known that the distance that a drug penetrates into the tissue after release depends on the relative rates of drug transport and drug elimination. When diffusion is the dominant transport mechanism, the concentration of the drug decays exponentially with distance from the implant. In many instances, only the tissue within a few millimeters of the implant is exposed to a therapeutically useful drug concentration. In this case, treatment may be enhanced by alternative delivery methods that increase the penetration distance of the drug into tissue and eliminate the rapid decay in concentration with distance that is characteristic of diffusion mediated transport.

Convection-enhanced drug delivery (CED) uses direct infusion of a drug-containing liquid into tissue so that transport is dominated by convection. By increasing the rate of infusion, the convection rate can be made large compared with the elimination rate in a region of tissue about the infusion point. Thus, CED has the potential of increasing the drug penetration distance and mitigating the decay in concentration with distance from the release point. In addition, CED may overcome limitations of traditional treatments for brain tumors caused by the large tumor size and the difficulty of delivering therapeutic agents into their dense tissue.

Convection-enhanced drug delivery has been tested extensively in animals and humans. Small molecules, proteins, growth factors, and nucleotides reportedly have been infused into animal models for therapeutic and imaging purposes. Chemotherapy agents, viral vectors, and proteins reportedly have been infused into humans in clinical trials. Initial studies reportedly were confined to infusion in the homogenous, gray matter bodies of the brain. Other published studies have concentrated on the globus pallidus internus, peripheral nerves, tumors, and the brainstem. The results of these studies indicate that convection can be used to distribute molecules, regardless of their size, throughout most regions of the brain. However, it can be difficult to control the distribution of infused molecules when characteristics of the tissue vary within the treatment region, such as in heterogenous tumors and near white matter tracts in the brain. Clinical trials for treating brain tumors have reported similar problems in tracking and predicting the distribution of infused chemotherapy agents.

CED involves inserting a small cannula or needle into an afflicted area and infusing drug or imaging solutions at a specified flow rate. This cannula is most often a stainless steel needle ranging from 20 to 32 gauge (ga) in size. In prior reported studies, flow rates ranged from 0.1 to 10 µL/min and were controlled with an external syringe pump. At flow rates greater than 1 µL/min, backflow of infused solutions up the outside of the needle shaft has been reported. Apparently, at sufficiently high flow rates, the tissue separates from the needle and injected fluid flows preferentially along the separation. Backflow reduces control over drug delivery because infused solutions can flow out of the brain or into highly permeable white matter tracts surrounding the infusion site. The separation that allows backflow can be controlled by adjusting the flow rate and the size of the needle. Another problem encountered with needles is an unexpectedly large pressure at the needle tip at the start of an infusion. The large pressure may indicate that the tip of the needle is partially or fully occluded when it is inserted into the brain.

Microneedles with on-chip flow meters and pumps provide fluid flow control and minimize reagent volume. The implantation of silicon devices has been extensively characterized for cortical neural prosthetics. Some implanted devices have recorded electrical signals for up to one year in vivo. Other neuroscience applications for which microfluidic devices may be useful include measuring cerebrospinal fluid flow, infusing neurotransmitters and neurotrophic factors, and studying addiction mechanisms. For example, L-glutamate is the most ubiquitous excitatory neurotransmitter in the mammalian central nervous system (CNS). Its presence has been linked with various brain disorders including Parkinson's disease, schizophrenia, stroke and epilepsy. The measurement of functional levels of L-glutamate in the CNS is thus of interest. Intracranial microdialysis is a widely reported technique used for measuring L-glutamate and other amino acids in CNS tissues in vivo. It involves identification of chemicals of interest in the dialysis sample by using modern analytical techniques such as HPLC, with electrochemical detection or fluorescent detection. There are questions, however, about the reliability of such measures for studies of release and uptake of neuronal glutamate. Poor spatial resolution and slow time resolution attributed to the technique may result in inadequate sampling of neurotransmitters with fast kinetics like L-glutamate. L-glutamate is reportedly thought to be rapidly removed from the extracellular space by glutamate transporters located on neurons and glia in order to maintain low and non-toxic extracellular levels. Reported recent advances in microdialysis, combined with capillary electrophoresis separation and quantitation, allow for sampling of L-glutamate every few seconds. However, there has been a need for advancements in technology to record glutamate dynamics, second-by-second, with a spatial resolution of microns analogous to electrophysiological recordings of neuronal activity.

Reported voltammetric techniques coupled with microelectrodes have shown promise for measuring changes of neurotransmitters such as L-glutamate in the extracellular space of the brain. However, the microelectrodes previously reported have suffered from problems associated with the size of the recording microelectrodes, the microelectrode response time and the lack of ability to mass produce the microelectrodes. Burmeister et al., *Journal of Neuroscience Methods*, 119 (2002) 163-171 report the refinement of a ceramic-based microelectrode fabricated using photolithographic techniques for rapid measures of L-glutamate in CNS tissues.

In regard to drug delivery techniques, many promising treatments for brain diseases involve nanoparticles as drug or gene carriers. The blood-brain barrier prevents most particles from penetrating into the brain, making intracranial infusions, or convection-enhanced delivery (CED), an attractive drug delivery strategy. However, transport of particles through the extracellular space of tissues is hindered by the large size of nanoparticles (10-100 nm), which are much larger than small molecule drugs or therapeutic proteins that more easily penetrate the brain extracellular matrix (ECM). Nanoparticles may be able to penetrate brain tissue provided that particles are less than 100 nm in diameter, are neutral or negatively charged, and are not subject to rapid elimination mechanisms.

The published literature reports studies of CED of liposomes in animal tumor models. Initial studies involving two sizes of liposomes showed that 40 nm liposomes distributed throughout the striatum of rats, but that 90 nm liposomes were confined to regions near the infusion point. Infusion of polystyrene particles showed similar effects of particle size. The distribution volume for 100 nm polystyrene particles was about half of that for 40 nm particles. The effective pore size of the extracellular matrix of gray matter has been estimated to be between 38 and 64 nm, which may explain why larger particles have difficulty moving through the ECM. Other factors also may limit the extent of particle penetration in the brain. Nanoparticles can be entrained in white matter and in necrotic zones of brain tumors. Liposomes can accumulate in and move through perivascular spaces. Transport through perivascular spaces is thought to be an important part of fluid removal from the brain. It has been suggested that preferential transport through the perivascular space is responsible for some of the side-effects reported from CED and gene therapy clinical trials.

It may be possible to increase the effective pore size and enhance the penetration of nanoparticles in tissue by selective enzymatic digestion of some ECM components. For example, Netti et al., *Role of extracellular matrix assembly in interstitial transport in solid tumors*, Cancer Res. 60 (2000) 2497-2503 reported a 100% increase in the diffusivity of IgG following collagenase treatment of xenografted tumors. Unlike most other tissues, the extracellular matrix of the brain has a low content of fibrous matrix proteins such as collagen. Brain ECM primarily consists of a family of proteoglycans called lecticans and the two components to which they bind, tenascins and hyaluronan (HA). These three macromolecules form a ternary structure in the extracellular space of the adult brain. HA serves as the structural backbone of the brain ECM, and highly charged chondroitin-sulphate proteoglycans (CSPG) side chains anchor the ECM to cells and blood vessels. HA and CSPG can be selectively degraded in the brain by hyaluronidase and chondroitinase, respectively. However, some hyaluronidases cleave glycosidic bonds in CSPGs as well as those in HA.

In view of the known related art, the inventors have recognized a need for, among other things, improving upon related art devices and techniques directed at CED of drugs; eliminating or mitigating the known problems and drawbacks associated with related art devices and techniques directed at CED of drugs; providing novel devices and techniques for CED of drugs; and, identifying and implementing applications for such novel devices and techniques directed at CED of drugs.

These and other objects, as well as benefits and advantages, provided by the various disclosed embodiments, will become more apparent to persons skilled in the art based on the following description and figures associated therewith.

SUMMARY OF THE EMBODIMENTS OF THE INVENTION

An embodiment of the invention is directed to a microfabricated, silicon-based CED device. The device comprises a silicon shank portion, at least one individual parylene channel disposed along at least a part of an entire length of the shank, wherein the channel has one or more dimensioned fluid exit ports disposed at one or more respective locations of the channel and a fluid (drug) input opening. The fluid input opening may be configured or adapted to be connected to a fluid reservoir and/or a pump and/or a meter and/or a valve or other suitable control device(s) or apparatus that supplies and/or delivers fluid (e.g., a drug) to the microfabricated device. According to an aspect, the device includes a handle to aid in the manipulation of the device. A distal end of the device may be pointed or otherwise appropriately shaped to aid in its penetration of tissue or other anatomical structure. According to an aspect, the one or more individual parylene channels and their associated delivery ports may be disposed on one or more surfaces of the shank. The microfabricated device may be essentially rigid or semi-rigid (i.e., flexible).

By way of an illustrative, non-limiting example, a microfabricated device according to an embodiment of the invention is used for CED of drugs to treat disorders of the brain and other neural tissue. When used in the brain, the device circumvents the blood-brain barrier (BBB) by infusing drugs under positive pressure directly into tissue. According to an illustrative aspect, the microfabricated device comprises a silicon shank that contains one or more parylene channels. The silicon shank provides rigidity for inserting the device into the brain; the one or more parylene channels conduct drug-containing fluid(s) along the shank under pressure and release the fluid(s) through an open port in the shank for dispersal into the brain. The device is an improvement over conventional stainless steel needle-type catheters that are currently used for CED of drugs. Enumerated exemplary advantages of the device include: 1) a smaller cross-sectional area compared with conventional needles used in CED; 2) less disturbance to tissue when inserted into the brain than conventional needles; 3) the elimination of backflow or reflux along the outside of the inserted part, which in turn, permits higher rates of drug delivery in the device compared with conventional needles; 4) minimal or no occlusion of the channel during insertion into the brain; 5) multiple parylene channels can be fabricated into the silicon shank, each conducting a distinct fluid (drug), which allows simultaneous, sequential, or programmed delivery of multiple agents; 6) the device has the potential to serve simultaneously as a drug delivery system and as a sensor-equipped probe to measure local tissue characteristics such as, but not limited to, pressure, pH, ion-specific concentrations, location, and other parameters.

Another embodiment of the invention is directed to a flexible microfabricated device for convection enhanced delivery of drugs. According to an aspect, the flexible microfabricated device comprises a parylene microprobe portion that is attachable to a support scaffold, which provides sufficient structural rigidity for insertion of the device into the target tissue. The device may comprise one or more drug delivery channels as well as a handle portion as referred to immediately above.

Another embodiment of the invention is directed to a "functionalized" microfabricated device for convection enhanced delivery of drugs. As used herein, "functionalized" means that the device is equipped with integrated electrodes and/or a sensor to detect and/or convey selective parametric information or other stimuli.

According to an exemplary embodiment, any of the foregoing microfabricated CED devices may be functionally attached to the distal end of a long, thin support structure such as a catheter or a needle in or on which a fluid attachment could be made to the fluid input port(s) of the attached microfabricated CED device. This may be especially advantageous in applications involving relatively thicker tissue penetration; e.g., insertion through a human skull/target tissue versus insertion through a rat skull/target tissue.

Another embodiment of the invention is directed to a convection enhanced drug delivery method. In various non-limiting aspects, the method may comprise the delivery of enzymes or other materials to modify tissue permeability and improve drug distribution in the targeted tissue. According to an aspect, the method is directed to enhancing penetration of a drug-containing nanoparticle into brain tissue, involving the enzymatic digestion of at least one brain extracellular matrix component and intracranial infusion of the nanoparticle into the brain tissue. According to a particular aspect, at least one enzyme may be immobilized to a surface of the nanoparticle during the step of enzymatic digestion. According to another aspect, the use of a multi-channel CED device as described herein according to the various embodiments provides the ability to deliver enzymatic and/or other materials that can, e.g., modify the drug delivery site, and therapeutic materials, in virtually any order, sequencing, and/or timing without the need to use different delivery devices and the potential complications involved in doing so.

Another embodiment of the invention is directed to a method for making a device for convection enhanced delivery of drugs.

These and other objects, advantages and benefits provided by embodiments of the invention will now be set forth in detail with reference to the detailed description and the drawing figures and as defined in the appended claims.

BRIEF DESCRIPTION OF THE DRAWINGS

FIG. 1 is a photographic of a microfluidic CED device according to an exemplary embodiment of the invention;

FIG. 2 is a photographic of a flexible microfluidic CED device according to an exemplary embodiment of the invention;

DETAILED DESCRIPTION OF THE EMBODIMENTS OF THE INVENTION

Figure 3:
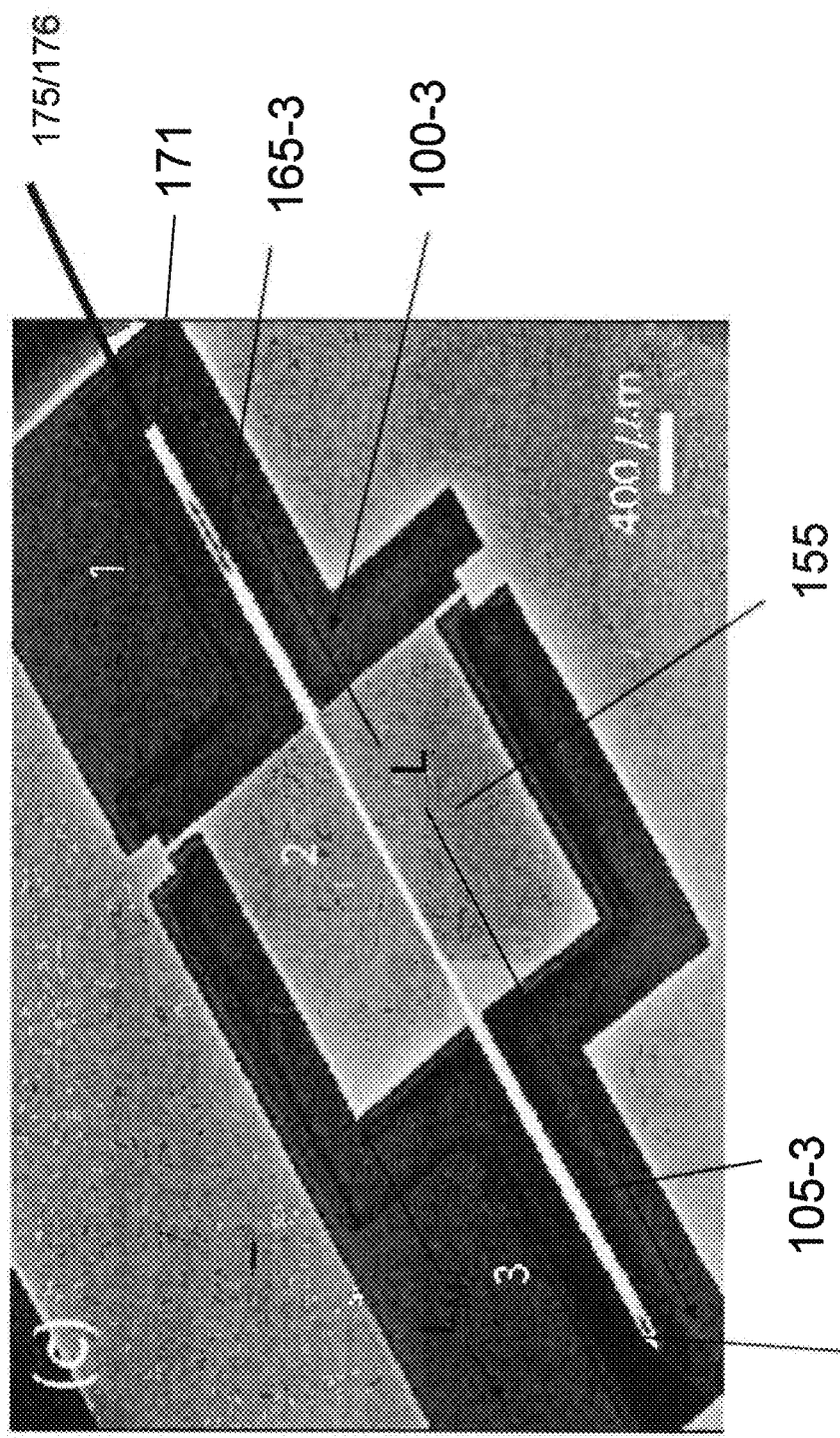
FIG. 3 is an electron micrograph of a microfluidic probe with protrusion for fluidic connection (1), base for handling (2) and tissue penetrating insert (3) according to an illustrative embodiment of the invention.

An embodiment of the invention is directed to a microfluidic, convection-enhanced-delivery (CED) device as illustrated by examples 100-1, 100-2, 100-3 in FIGS. 1, 2, and 3, respectively. With illustrative reference to FIGS. 1, 4, 5 and 6, the CED device 100-1 includes a layered-construction shank portion that includes a microprobe component 105-1 comprising a silicon substrate 112, a polyimide layer 116, and a parylene (e.g., parylene A, C, N) layer 120 (FIG. 5). The CED device has at least one parylene, laminar flow channel 125 disposed therein along at least a portion of a total length L of the device as shown in FIG. 3. The at least one channel has at least one fluid outlet port 127 as further shown by example, in detail, in FIGS. 4 and 6. The microprobe component 105 of the CED device 100 has a distal end 130 having an anatomically-compatible shape 131 (e.g., pointed for penetration) as shown in FIG. 4, to aid in penetrating or otherwise accessing the device insertion site of the targeted tissue, e.g., brain or other tissue.

As further illustrated in FIGS. 1-3, the device 100 includes a handle portion 155-n connected to the microprobe component 105 and a fluid supply portion 165-n. The fluid supply portion has at least one respective channel 167 fluidly connected to the at least one channel 125 in the microprobe component. The at least one respective channel 167 in the fluid supply portion has an inlet port 171 that is connectable to a fluid supply 175 (therapeutic and/or other) and an external pump, valve, meter, or other delivery controller 176 as schematically shown in FIG. 3.

Figure 4:
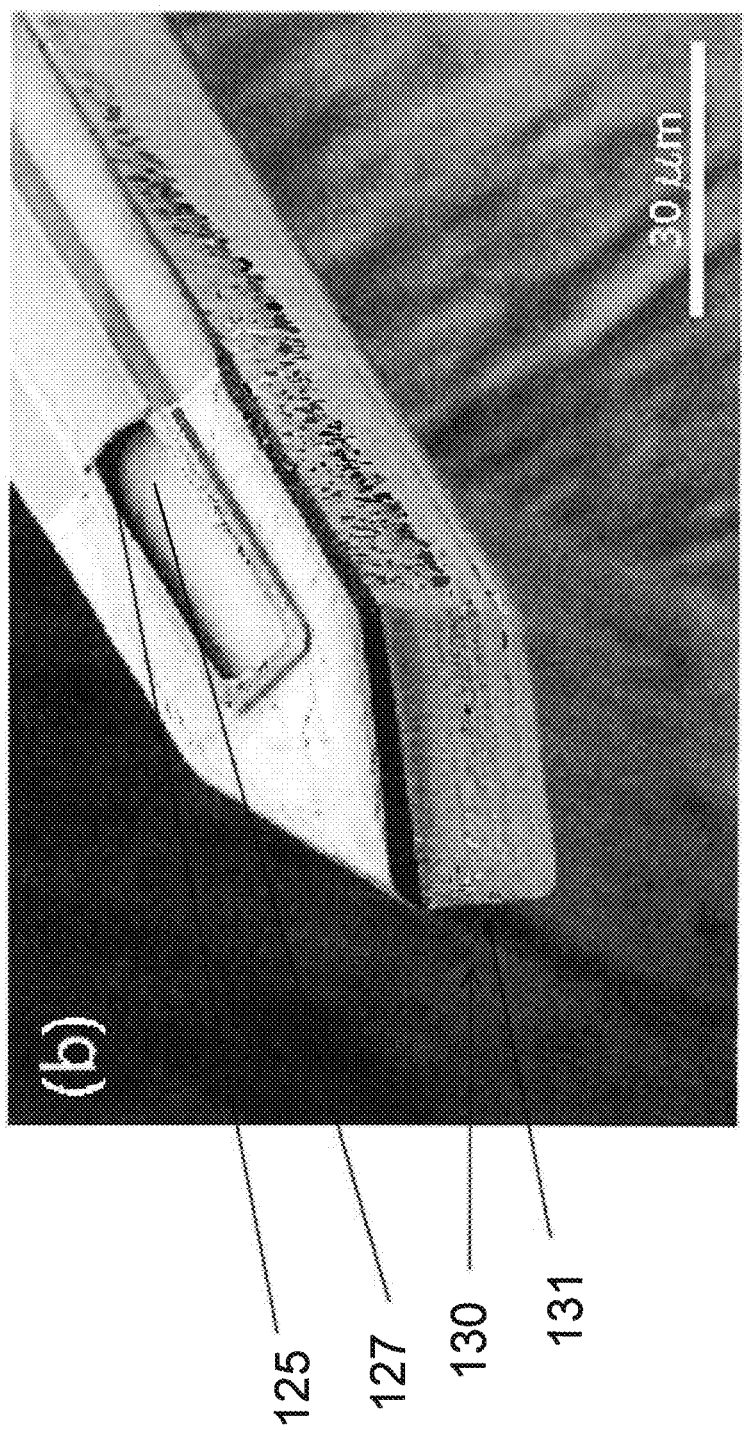
FIG. 4 is an electron micrograph of the pointed tip of an insertable portion of a microprobe according to an illustrative embodiment of the invention.
Figure 5:
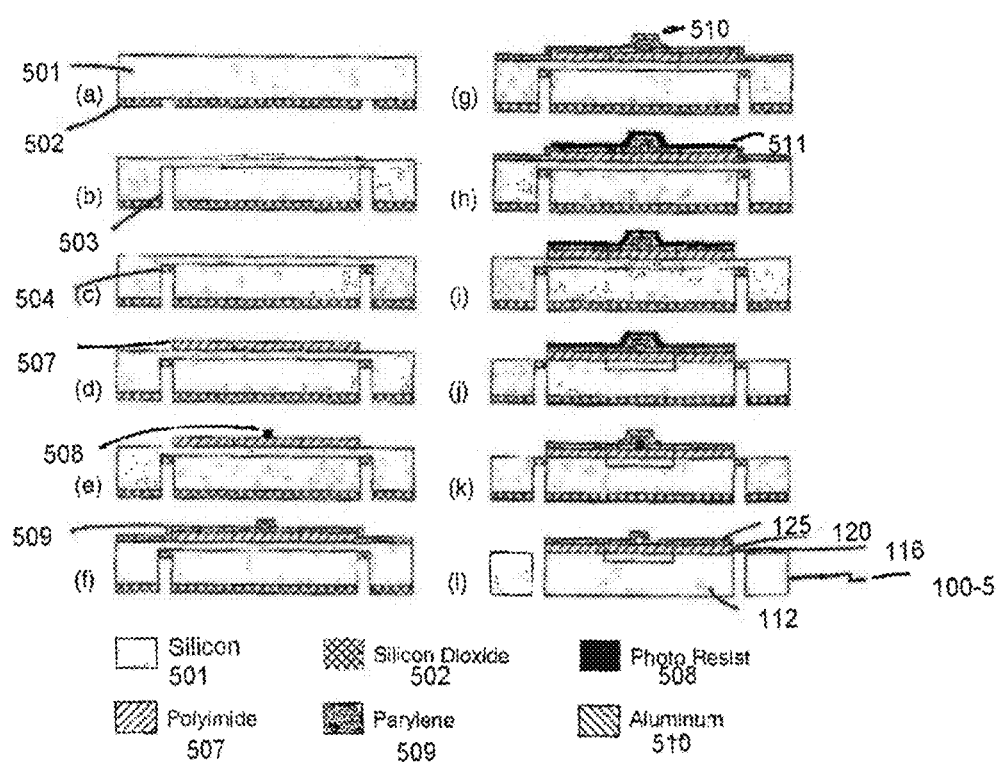
FIGS. 5(a-l) are schematic cross sectional drawings illustrating a microfabrication process of an exemplary CED device according to an exemplary embodiment of the invention.

As illustrated for example in FIG. 4, the at least one parylene channel is disposed in a top surface of the microprobe component 105. In various aspects, the at least one parylene channel could be disposed in more than one surface of the microprobe component and, as will be described in greater detail below, two or more separate channels may be disposed on respective surfaces of the microprobe component or side-by-side on one or more of the surfaces.

According to various exemplary aspects, the cross sectional, diametrical dimension of the microprobe component will advantageously be equal to or less than 0.2 mm; the microprobe component will advantageously have a length $L_M$ of between about two millimeters to about 50 mm and a cross sectional area of between about 1,000µ² and 20,000µ²; the at least one channel will advantageously have a height $h_C$ of between about one micron to about 50µ and a width $w_C$ of between about 10µ to about 100µ.

Figure 7:
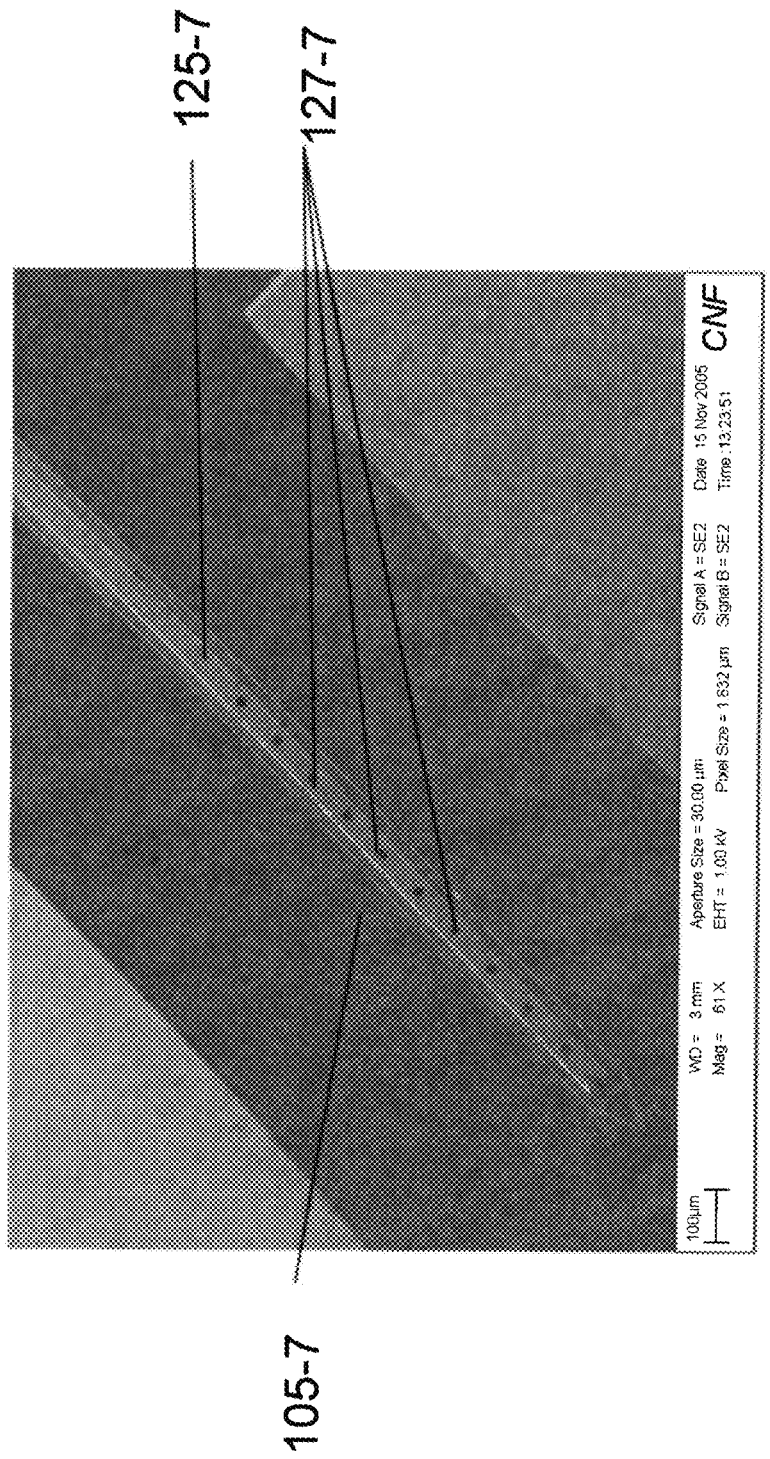
FIG. 7 is a photomicrograph of the microprobe component of a CED device having multiple outlet ports disposed along the length of the probe according to an exemplary embodiment of the invention.

According to an exemplary aspect of a CED device as illustrated in FIG. 7, the microprobe component 105-7 includes a channel 125-7 that has a plurality of fluid outlet ports 127-7 disposed in a surface of the microprobe component as shown.

The target tissue-insertable microprobe component of the CED device embodiments may have a functionalized coating such as, e.g., an albumin coating.

Figure 8:
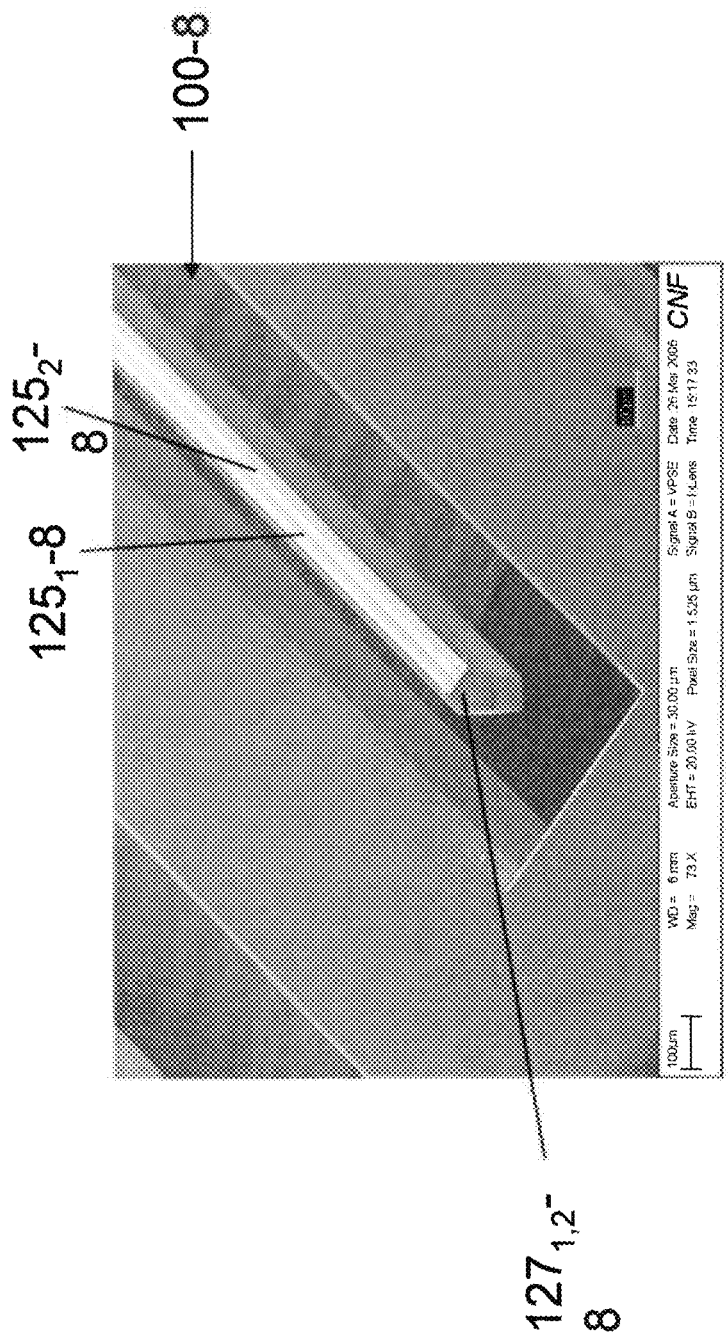
FIG. 8 is a photomicrograph of the microprobe component of a CED device having two parallel channels having outlets at 0.5 mm from the tip according to an exemplary embodiment of the invention.

As mentioned above, the CED device may have more than one channel. A microfluidic, CED device 100-8 wherein the microprobe component has two, adjacent parylene channels $125_1$-8, $125_2$-8 is illustrated in FIG. 8 according to an exemplary aspect of the invention. As will be described in greater detail below, a multiple (e.g., two) channel device could be used for an advantageous drug delivery protocol where, for example, an agent that increases target tissue drug permeability (e.g., an enzymatic or hyperosmolar solution) could be delivered through one of the channels and a therapeutic agent could be delivered through another of the channels. Delivery of the multiple agents could be made simultaneously, sequentially, or programmed in any desired manner to achieve a particular effect.

Figure 9:
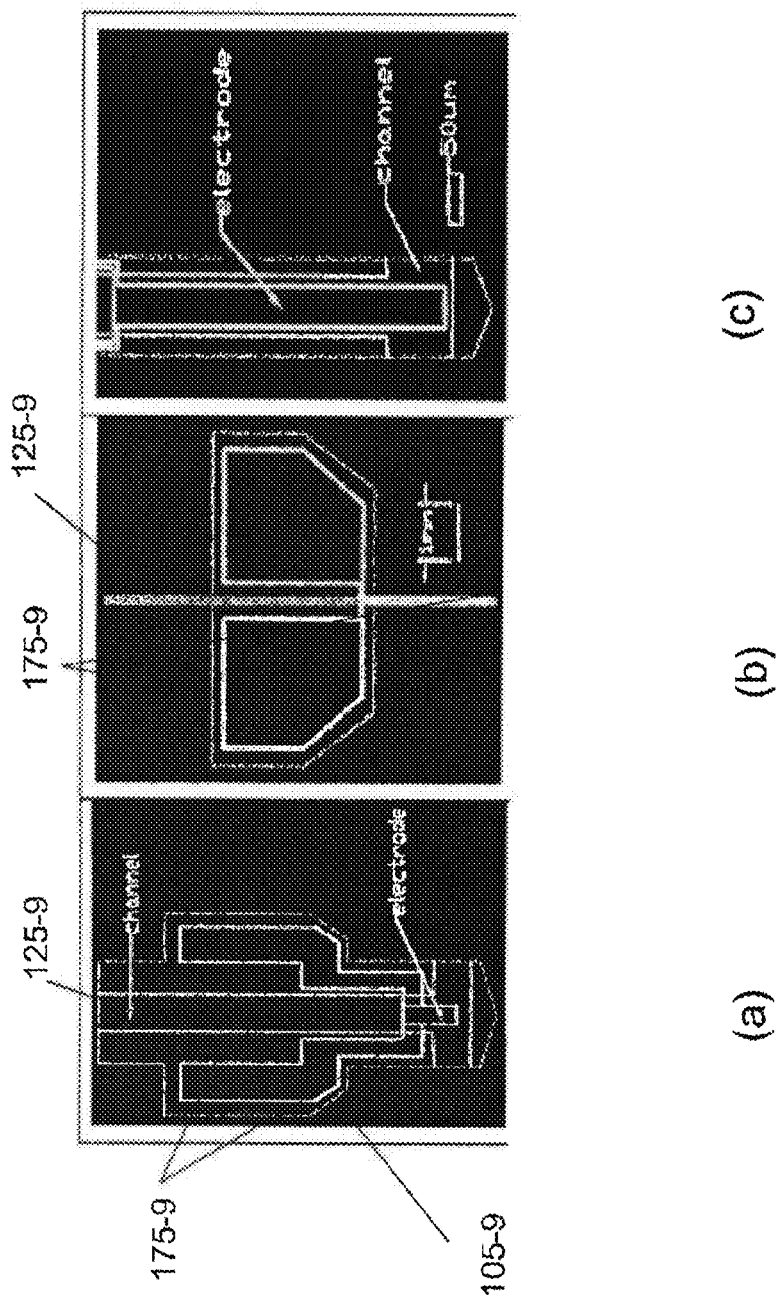
FIGS. 9(a-c) are schematic profile drawings showing a CED microprobe with integrated electrodes according to an exemplary embodiment of the invention.
Figure 10:
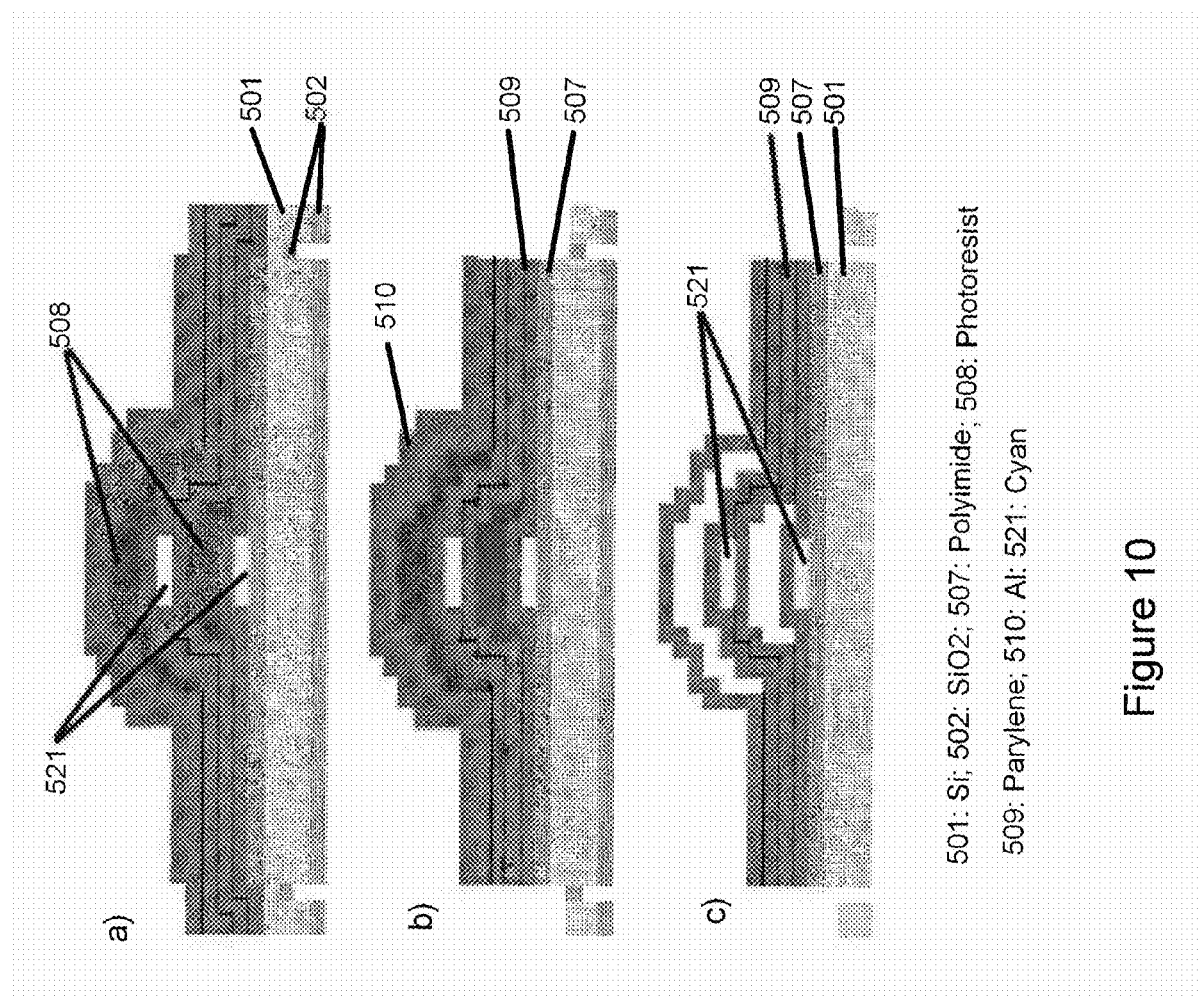
FIGS. 10(a-c) are schematic cross sectional drawings illustrating a microfabrication process of an exemplary CED device according to an exemplary embodiment of the invention.

According to an exemplary embodiment as illustrated in FIGS. 9(a-c), the CED device 105-9 may also be further functionalized by incorporating a stimulating or a recording electrode 175-9 into the tissue-penetrating microprobe component 105-9 of the device. FIG. 10(a-c) schematically show the fabrication layers of an exemplary CED device with integrated electrodes.

An exemplary embodiment of the CED device incorporates a sensor in the microprobe component of the device. Various types of sensors may be integrated to functionalize the device in addition to its drug delivery attributes. For example, these may include, generally, an interrogatable sensor; more specifically by example, a pH sensor, a temperature sensor, an ion concentration sensor, a carbon dioxide sensor, an oxygen sensor and, by non-limiting example, a lactate sensor or a glutamate sensor.

With further reference to FIGS. 9(a-c) and 10(a-c), an exemplary process for making a glutamate sensor involves patterning metal recording electrodes 175-9 on the microfluidic probe body 105-9 using a metal lift-off procedure. After the fluidic probe is complete, a layer of photoresist is applied and patterned using a bright field mask. Before developing, this layer is placed in an image reversal oven in a NH$_3$ atmosphere and flood exposed using a UV lamp. Once this layer is developed, the wafer will be coated with photoresist everywhere except where the electrodes will be deposited. Next, a chrome adhesion layer (50 nm) and a layer of gold (250 nm) are deposited on the wafer using E-beam evaporation. The resist underneath the metal layers is then removed to leave the metal films that form the electrodes. Once the electrodes have been formed, a layer of parylene is deposited to insulate the electrical connections. This insulating layer is coated with a film of aluminum, which is in turn patterned using photolithography and wet etching to create an etch mask. The wafer is then patterned in an O$_2$ plasma to open the recording and bonding pads. Once the electrodes have been patterned, and the channels have been cleared of photoresist, the channels are back-filled with hot poly-ethylene glycol (PEG) to keep them from being blocked during the subsequent fabrication steps, which have been adopted from Burmeister et al., *Improved ceramic-based multisite microelectrode for rapid measurements of L-glutamate in the CNS*, Journal of Neuroscience Methods, 119 (2002) 163-171. First, the devices are dipped in a Nafion® solution (5% in aliphatic alcohols) and dried. Next, the devices are dipped in an aqueous solution containing 1% glutamate oxidase, 1% BSA, and 0.125% glutaraldehyde, and again allowed to dry. Any PEG that is remaining in the channels can then be removed in an aqueous bath, leaving devices with both glutamate sensors and microfluidic channels.

Figure 11:
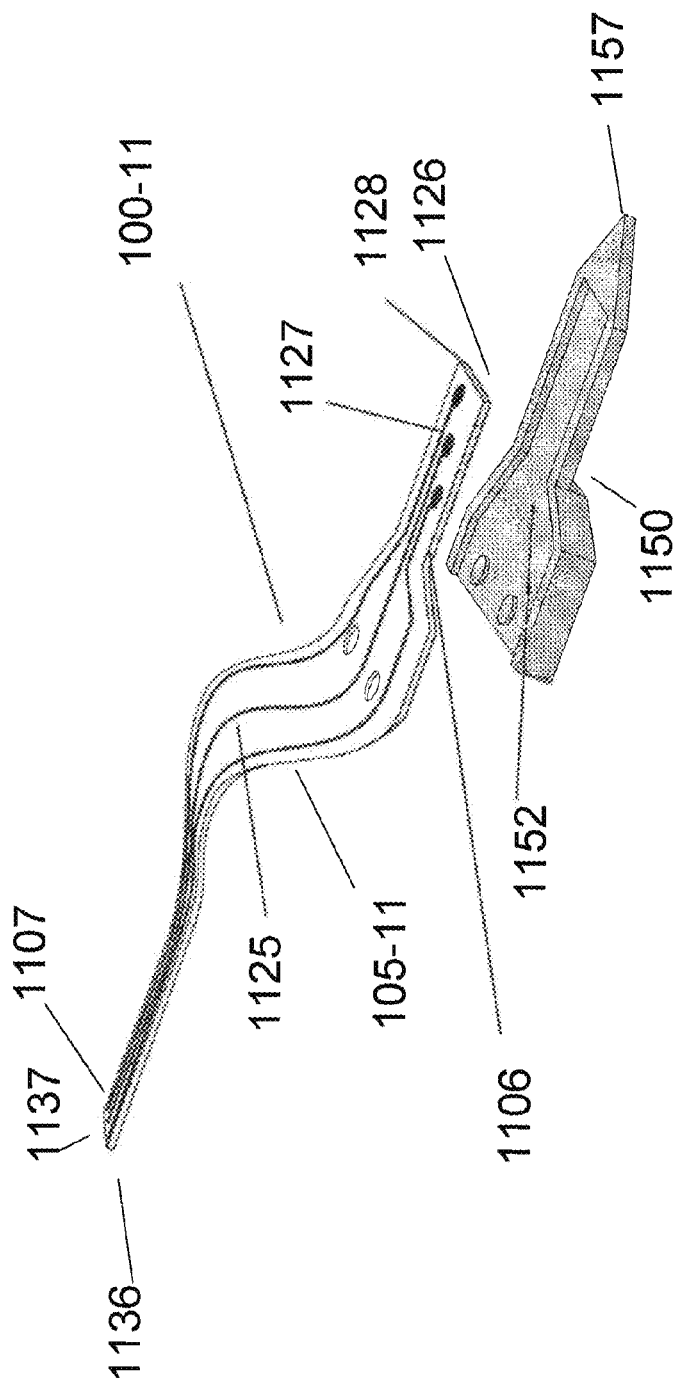
FIG. 11 is a schematic diagram showing a flexible parylene CED microprobe and an associated insertion scaffold according to an exemplary embodiment of the invention.

An exemplary embodiment of a flexible microfluidic CED device 100-11 is schematically illustrated in FIG. 11. The exemplary device comprises a flexible parylene microprobe body 105-11 having an implantable shank portion 1106 and a fluid inlet portion 1107 that is contiguous with the shank portion. The device has at least one parylene composition channel 1125 (three as shown in the figure) disposed in a length of the device. The at least one parylene channel has a proximal end 1137 at a proximal end 1136 of the fluid inlet portion and a distal end 1128 adjacent a distal end 1126 of the implantable shank portion. The at least one parylene channel 1125 has at least one outlet port 1127 (three as shown in the figure), which is at the terminal distal end of the channel. According to an alternative aspect referred to above (see FIG. 7), each channel may have one or more outlet ports disposed at various locations in the channel as may be appropriate for particular application served by the CED device.

Further illustrated in FIG. 11 is an insertion support scaffold 1150 that is attachable to the device 100-11. The insertion support scaffold is advantageously used in conjunction with the flexible device in the event the device is too flexible to support its insertion into target tissue. The support scaffold as shown has a shelf portion 1152 configured to retain at least the implantable shank portion 1106 of the flexible microprobe body, and a distal end 1157 having an anatomically-compatible shape (e.g., pointed) for tissue penetration or navigation. According to alternative exemplary aspects, the at least the implantable shank portion 1106 of the flexible microprobe may be fastened to the shelf portion of the scaffold via surface tension from a water drop, various glues, or a biocompatible petroleum jelly.

According to the exemplary aspect, the support scaffold 1150 is constructed from a degradable thermoplastic polymer, for example, a degradable thermoplastic polyester or a degradable thermoplastic polycarbonate. According to a particular aspect, the insertion support scaffold is made of poly(lactic-co-glycolic acid) (PLGA). Thus, once inserted, the scaffold will biodegrade within the target tissue, eliminating the need to remove it and possibly dislodging the CED device.

The insertion support scaffold may additionally contain a quantity of a drug and/or a surface of the insertion support scaffold may be coated with a drug or other functional agent. Exemplary agents may include anti-inflammatory components, drug permeability-increasing components, and others.

In an exemplary system embodiment, the flexible CED device will be appropriately connected to a fluid supply at the proximal end of the fluid inlet portion. The system may incorporate a controllable fluid supply generator connected to the fluid supply such as a programmable pressure generator or a programmable flow-rate generator, and various control components such as pumps, valves, meters, and/or other microfluidic components.

Further non-limiting, exemplary and illustrative embodiments of the invention will now be described with reference to demonstrative and investigative data, device fabrication, drug administration applications, and related information obtained via experiments involving rat brains. Due to the relatively small dimensions of rat skulls, exemplary microprobe component length dimensions are correspondingly small. However, for applications involving relatively larger target tissue dimensions (e.g., human or other large animal skulls/brains or other tissue/organs), a longer microprobe portion and/or deeper tissue penetration depth may be necessary. The use of a longer microfabricated, microprobe portion may not be feasible due to insufficient structural rigidity. This situation is addressed according to an exemplary embodiment of the invention schematically illustrated by apparatus 1500-1 in accordance with FIG. 15. At least the microprobe portion 1501 of a microfabricated CED device is attached to a distal end of a thin, elongate support structure 1503 having a length that is necessarily greater (e.g., 2x) than the microprobe portion length $L_M$, which may advantageously be in the form of a catheter or a needle of appropriate gauge and having an appropriate bore 1505 in fluid connection with the microchannel(s) of the CED device (or at least the microprobe portion) to transport fluid thereto. The dotted line 1507 represents the thicker target tissue (e.g., skull, brain, organ, etc) depth of a relatively larger subject (e.g., human) in contrast to the relatively smaller dimension shown by the illustrative rat brain 1506. The longer catheter/needle structure will accommodate penetration deeper into target tissue as necessary to reach the target with the microprobe portion without risking microprobe breakage or other failure mechanisms possible with a longer microprobe portion per se. According to an exemplary aspect, the elongated support structure may substitute for the fluid supply portion of the CED device or be in addition thereto. The bore of the support structure can be connected to a fluid supply/controller as described above by microtubes or other known apparatus.

Exemplary method embodiments for making microfluidic CED devices as set forth herein will now be described.

A practical first step in building an integrated microfluidic delivery system for CED according to the embodiments of the invention was to demonstrate that fluid can be delivered through a microfabricated device at rates comparable to those for needles and cannulas. The exemplary embodiments that follow describe the microfabrication and testing of a device that can be inserted into brain tissue and deliver flow rates appropriate for CED (e.g., 0.1-5 µL/min). The illustrative device was designed to deliver fluid to the caudate nucleus of adult rats for direct comparison with previous studies that used needles. Infusions into agarose brain phantoms and the rat caudate were examined to determine whether higher flow rates could be achieved, without significant fluid reflux, with microfluidic devices than with standard needles. In addition, an analytical model was developed to examine the effect of diffusion on the penetration of infused drugs.

Fabrication of Microfluidic Probes

Figure 6:
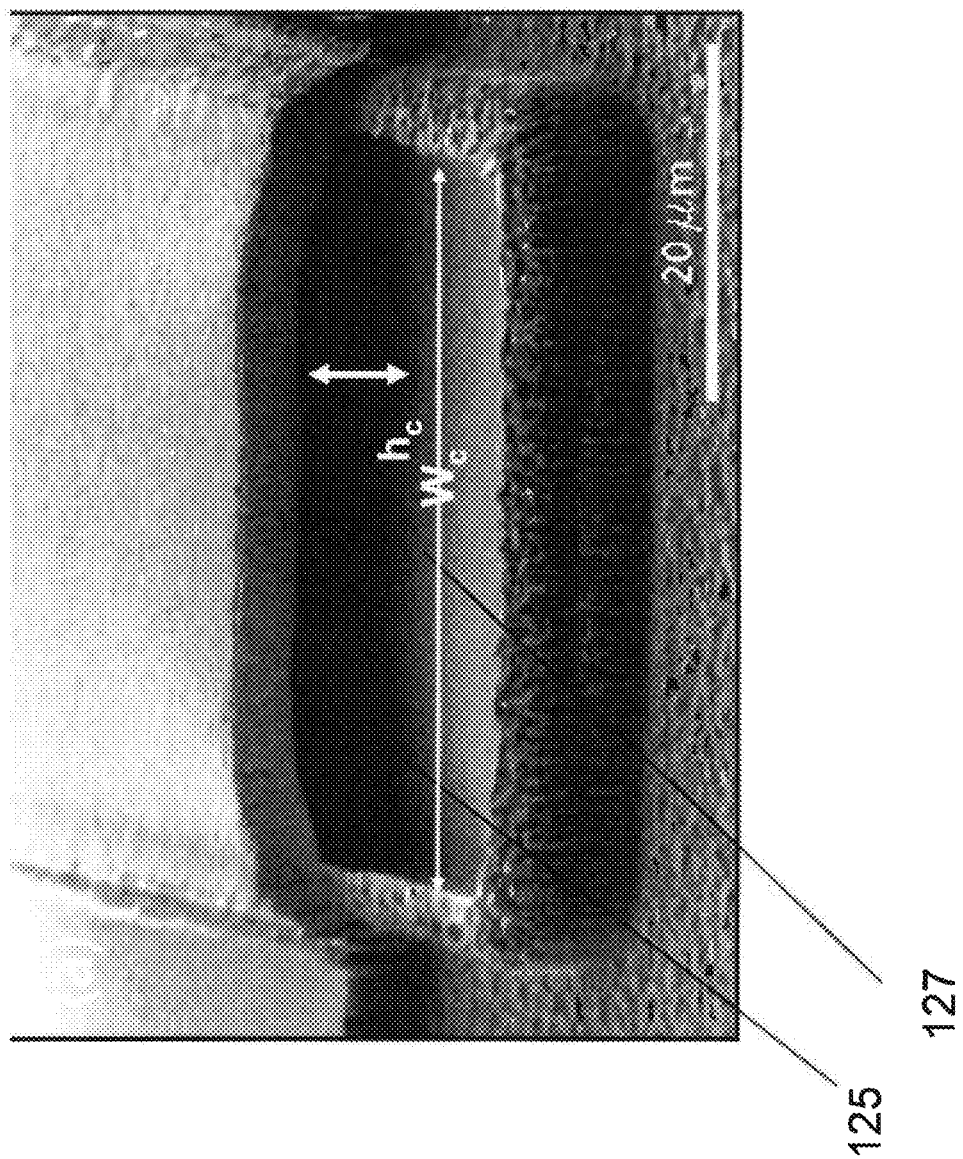
FIG. 6 is an electron micrograph of a parylene microfluidic channel with dimension of 50×10 μm in the device shown in FIG. 4 according to an illustrative embodiment of the invention.

With reference to FIGS. 5(a-l), an exemplary device was fabricated using standard micromachining techniques for patterning silicon and polymer layers. FIG. 5 shows a schematic of the fabrication process, which involves a series of patterning, deposition, and removal steps. The finished device consists of three parts as shown in FIGS. 3, 4, and 6: an insertable microprobe portion 105 with a cross-section of 100×100 µm and a length that varies from 2 to 5 mm, a handle portion 155 with dimensions of 2 mm×2 mm×300 µm, and a fluid supply portion 165 with a length of 2 mm and a cross-section of 100×100 µm that can be connected to external tubing.

To start the fabrication a silicon dioxide etch mask 502 was deposited on the backside of a double-sided, polished silicon wafer 501 with a thickness of 30 µm (FIG. 5(a)). The backside of the wafer was then etched with deep reactive ion etching to a depth of 200 µm to define the insert and protrusion thickness 503 (FIG. 5(b)). A 2 µm silicon dioxide layer 504 was then deposited on the backside of the wafer using plasma enhanced chemical vapor deposition (PECVD). This layer acts as an etch stop when the front side of the wafer is etched in a subsequent step (FIG. 5(c)).

A 5 µm thick layer of positive tone polyimide 507 (Photoneece, Toray Industries, Japan) was spun, patterned, and cured on the front side of the wafer to form a base layer for the microchannel (FIG. 5(d)). Next, sacrificial photoresist was spun on top of the polyimide to form a layer 508 of height 10-15 µm. The wafer was then soft-baked in a convection oven at 90° C. for 30 min. The photoresist was patterned and developed, leaving photoresist in place to define the microchannel (FIG. 5(e)). The assembly was hard-baked at 90° C. for 5 min. The polyimide base layer was then roughened with an oxygen plasma (400W, 1 min) to promote adhesion between polyimide and parylene. A layer of parylene C (Specialty Coating Systems) was then deposited to a thickness of 5 µm (FIG. 5(f)).

Following parylene deposition, a 100 nm layer of aluminum 510 was electron beam evaporated and patterned in the shape of the channels (FIG. 5(g)). The aluminum acts as a mask for etching the inlet and outlet holes of the channel. A subsequent resist layer 511 was spun and patterned to serve as an etch mask for both the bulk parylene etch and the silicon deep reactive ion etch (FIG. 5(h)). Parylene was etched with 150 W oxygen plasma at a rate of 100 nm/min (FIG. 5(i)). The silicon was etched down to the oxide etch stop to define the insert and protrusion geometry (FIG. 5(j)). Next, the inlet and outlet holes were etched in the parylene layer using the aluminum etch mask (FIG. 5(k)). The oxide etch stop and aluminum mask were simultaneously removed in buffered oxide etch. Finally, the photoresist was removed from the channels in an acetone bath for 4 hours followed by 4 hours in isopropyl alcohol and 12 hours in deionized water (FIG. 5(l)).

This procedure was used to fabricate channels with heights between 1 and 20 µm and widths between 10 and 100 µm. The channels in the exemplary device had a height of 10 µm and a width of 50 µm (FIG. 6). The length of the channel was 8 mm running from the fluid supply portion to the tip of the microprobe portion.

Figure 12:
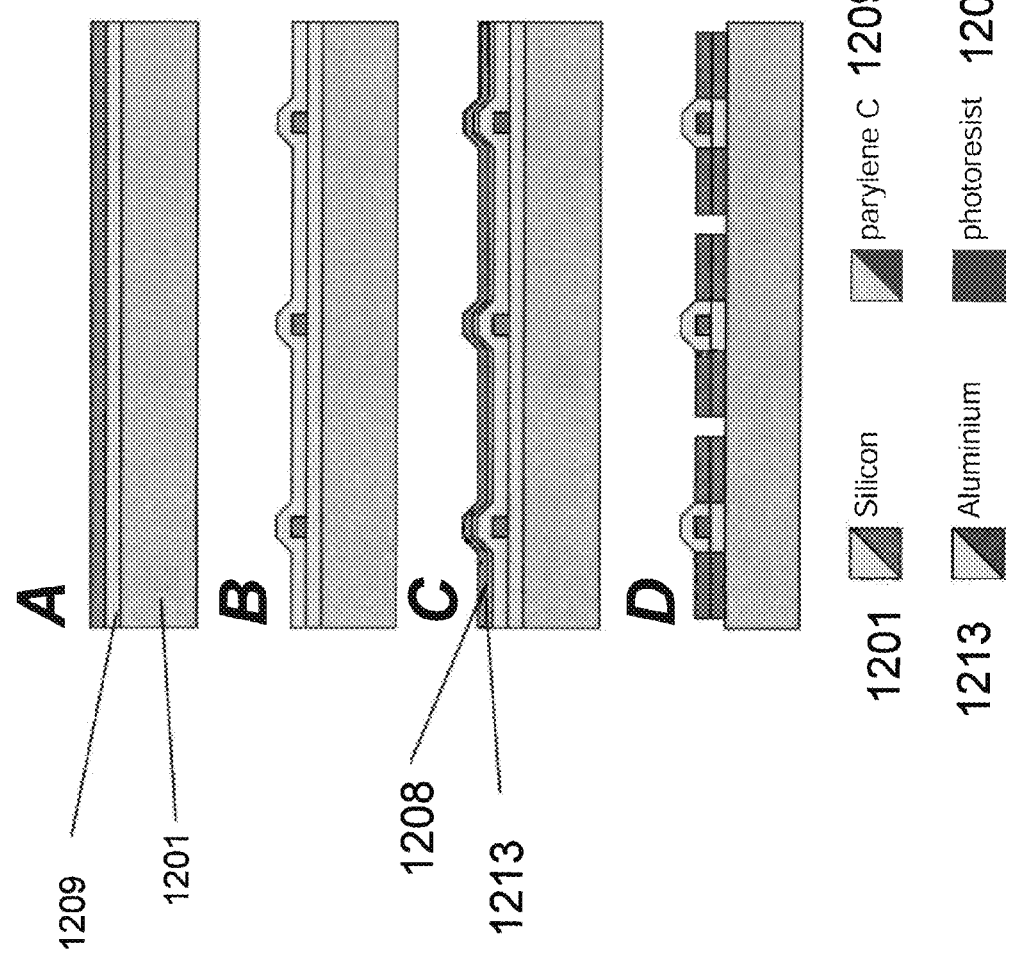
FIGS. 12(A-D) are schematic cross sectional drawings illustrating a microfabrication process of an exemplary flexible CED device according to an illustrative embodiment of the invention.

According to an exemplary aspect as illustrated in regard to FIG. 12, a method for making a flexible, microfluidic CED probe includes the steps of depositing a layer of parylene 1209 onto a prepared silicon wafer 1201 (FIG. 12(A)); applying a selected depth of photoresist 1208 onto the silicon wafer corresponding to an intended height of a channel (FIG. 12(B)); patterning the photoresist layer to define an inside region of the channel; forming a top region of the probe by depositing a second layer of parylene 1210 onto the wafer; depositing an etch mask onto the wafer; patterning the etch mask in order to define the overall shape of the probe (FIG. 12(C)); etching through the parylene layer to the silicon wafer to define the probe body (FIG. 12(D)); removing the resist from the inside region of the channel; and removing the finished probe from the wafer.

According to an exemplary aspect, a method for making an insertable support scaffold (e.g., 1150, FIG. 11) for a flexible, microfluidic CED probe (e.g., 100-11, FIG. 11) involves the steps of providing a suitable mold having a mold shape for the finished scaffold; loading an appropriate quantity of a thermoplastic polymer into the mold shape; pressing and heating the loaded mold such that the thermoplastic polymer is heated to above its glass transition temperature $T_g$; cooling the mold to below $T_g$; and, removing the finished scaffold from the mold. According to a particular exemplary aspect, the method comprised loading an appropriate quantity of poly(lactic-co-glycolic acid) (PLGA) into the mold shape.

According to an exemplary aspect, a method for making a molecular-targeted CED-based sensor involves the further steps of depositing and patterning an electrode and electrical connection onto the probe; depositing an insulating layer of parylene over the electrode and electrical connection; selectively etching the parylene layer to expose the electrode; applying an ion-conducting polymer to the electrode; and immobilizing an oxidoreductase specific to a target molecule to the electrode. According to a particular aspect, the method comprises dipping the device in a Nafion solution (5% in aliphatic alcohols) and drying. According to a particular aspect, the method comprises dipping the device in an aqueous solution containing glutamate oxidase, BSA, and glutaraldehyde.

Experimental Set-up

Fabricated microfluidic devices were attached to micropipettes (OD=1 mm, ID=0.58 mm and OD=2 mm, ID=1.12 mm) using two part epoxy. The micropipette was then backfilled with 0.1% (w/v) Evans Blue, or 1% (w/v) Evans Blue labeled albumin, and inserted into a micropipette holder on a micromanipulator. The micropipette holder was connected to a programmable pressure injector (World Precision Instruments PM8000, Sarasota, Fla., USA) with low compliance polyethylene tubing. Compressed high purity nitrogen was used as a pressure source. The injector maintained a constant pressure at the inlet of the channel. The flow rate through the devices was determined by measuring the speed of the liquid front in the micropipette. In some experiments a 30 ga blunt needle was used in place of the microfluidic device so that a direct comparison could be made between delivery methods.

While typical CED protocols infuse fluid at a constant flow rate, infusion at constant pressure was found to be particularly advantageous. It was easier to manipulate fluid in the microfluidic devices by regulating pressure rather than flow rate, especially while priming a channel that is initially filled with air. Moreover, in constant pressure infusion, the pressure profile in the tissue exhibited independence from tissue material properties.

Agarose Brain Phantoms

Agarose gels (0.6% w/v) were used as a brain tissue analog to characterize the delivery from the devices. Flow in agarose at this concentration has been shown to mimic some characteristics of pressure-driven flow in brain tissue. Agarose powder was added to Tris-Borate-EDTA (TBE) buffer and heated in a microwave oven on high heat for 90 seconds while covered. The hot solution was poured into 100 mm tissue culture plates and allowed to gel for 2 hours at room temperature. The devices were inserted 5 mm into the gels at a rate of 1 mm/s using a micromanipulator. A fixed volume (ranging from 10 to 4 µL) of the dye solution was infused into the gel at pressures of 35, 70, 140, and 210 kPa.

The dye flowed radially outward from the tip of the device and formed an approximately spherical volume about the device tip. After infusion, which lasted between 10 and 80 minutes, the penetration depth was determined by measuring the diameter of the dyed agarose sphere with calipers.

Animal Studies

Twelve male Sprague-Dawley rats (180-200 g) were used to characterize the performance of devices in vivo. The rats were anesthetized with ketamine (100 mg/kg)/xylyzine (10 mg/kg) solution via intraperitoneal injection. The head was shaved and disinfected with butadiene/alcohol/butadiene cotton swabs. An incision was made and a 1 mm diameter hole was drilled in the skull 3 mm laterally from bregma. The device was inserted into the brain at a rate of 1 mm/s with a micromanipulator.

The tissue was allowed to equilibrate mechanically for 3 minutes. Then, a solution Evans Blue labeled albumin was infused at 35, 70, and 140 kPa into the caudate putamen. The flow rate was determined by measuring the fluid speed in the micropipette. After 5 µL of the Evans Blue labeled albumin solution was infused, the device was vented to atmosphere and promptly removed. The animals were immediately sacrificed by carbon dioxide inhalation and the brains were removed and flash frozen in −70° C. hexane. The brains were sectioned into 25 µm slices on a cryostat. Every fifth slice was collected for image analysis. All procedures were done in accordance with the regulations of the Yale University Institutional Animal Care and Use Committee.

Image Analysis

Frozen sections of brain tissue sections were imaged using a stereoscope and CCD camera. Images were captured as RGB 8-bit TIFF files using StreamPix software (Norpix Inc., Montreal, Canada). To determine the penetration of the albumin, the RGB file was broken into red, green, and blue planes using a Matlab script. Each plane consists of 480×640 pixels of intensity data on a scale of 0-255. Blue plane pixels were normalized by dividing each individual pixel by the total pixel intensity of all three colors, BN=B/(R+G+B). A pixel was considered to have a dominant blue intensity if the value of BN was greater than 0.333. Pixels with values greater than 0.333 were assigned a pixel value of zero, and all pixels with values less than 0.333 were assigned a value of one. The result was binary image where zero is black and one is white. To minimize background noise an erosion operation was applied to each image. The erosion operation specified that if more than four of a black pixel's eight neighbors were white, then that pixel was changed to white. The topology of the thin slices left artifacts in the image that appeared as isolated white pixels within large black, or dyed, areas. A dilation operation was used that specified if more than four of a white pixel's eight neighbors were black, then that pixel was changed to black. After image processing, the area of each slice was calculated by summing the number of black pixels. The Analyze Particles tool in ImageJ software (National Institutes of Health, Bethesda, Md.) was used to calculate the area of each dye spot and the major and minor axis of an ellipse fit to the spot. Because we were interested in examining drug delivery in gray matter, only dye in the gray matter was considered for calculating the aspect ratio between the major and minor axis. This method does not measure dye concentration, but instead determines only a threshold concentration. Some of the images from each animal were also imaged by epifluorescence using a rhodamine filter to estimate the threshold concentration. A two dimensional surface plot of the intensity profile of the fluorescent images was compared to processed stereoscope images. Assuming that intensity is proportional to concentration, the threshold concentration was approximately 60% of the injected concentration.

Model of Fluid Transport

Fluid transport during infusion into gels and tissue depends in part on the mechanical response of the medium to the imposed flow. Models have been developed to describe fluid transport in rigid pore, poroelastic, and poroviscoelastic models of the medium. Including poroelastic or poroviscoelastic properties in a model is useful for capturing transient responses of the matrix and the time-dependent stress in the matrix. At steady-state, though, the pressure and velocity fields are independent of the particular constitutive assumption for the material. That simplification is exploited here to estimate an apparent hydraulic permeability of the medium and a penetration distance that incorporates the role of diffusion.

Mass conservation of the tissue solid matrix and fluid constituents can be expressed as $$\nabla \cdot (\phi v + (1-\phi)\partial u/\partial t) = 0 \quad (1)$$

where v is the fluid velocity vector, u is the solid matrix velocity vector, and $\phi$ is the porosity. Darcy's law gives the following relationship between velocity and pressure in porous media $$\phi(v - \partial u/\partial t) = -\kappa \nabla P \quad (2)$$

where $\kappa$ is the hydraulic permeability and P is the pressure. Assuming steady state and purely radial flow, Eq. (1) becomes $$(1/r^2)(\partial/\partial r)(r^2 v_r) = 0 \quad (3)$$

which is integrated to obtain $$v_r = A/r^2 \quad (4)$$

Substituting Eq. (4) into Eq. (2) and integrating yields $$P(r) = (\phi A/\epsilon r) + B \quad (5)$$

The integration constants A and B are found by assuming that the pressure decreases to zero at infinity and that $P(a)=P_0$, where $P_o$ is the pressure inside a fluid-filled cavity of radius a about the tip of the microfluidic channel. Evaluating the constants gives the following pressure and velocity profiles $$(P(r)/P_o) = a/r \quad (6)$$

$$v_r(r) = P_o \kappa a/\phi r^2 \quad (7)$$

The volumetric flow rate at the channel tip is $$Q(a) = \phi v_r(a) 4\pi a^2 = 4\pi a \kappa P_o \quad (8)$$

In the experiment, the flow rate, Q(a), is measured for various values of the pressure $P_o$. Eq. (8) suggests that a plot of $Q(a)/4\pi a$ as a function of $P_o$ should give a straight line with a slope that is an apparent permeability of the medium.

The penetration distance of an infused compound can be estimated by assuming that convective and diffusive transport take place in parallel. The characteristic time for diffusion, $\tau_D$ is, $$\tau_D = r^2/D \quad (9)$$

where D is the diffusion coefficient of the infused molecules in the porous medium. The characteristic time for convection, $\tau_c$ is $$\tau_C = \int_a^r dr'/v(r') = (\phi/3P_0\kappa a)(r^3 - a^3) \quad (10)$$

To estimate the penetration distance after infusion over some time T, the inverse characteristic times for diffusion and convection are summed as follows $$1/T = 1/\tau_D + 1/\tau_C \quad (11)$$

The value of r that satisfies Eq. (11) is an estimate of the penetration distance R.

The Peclet number $Pe = \tau_D/\tau_c$ gives the relative importance of convective transport compared with diffusive transport. For infusion into a porous medium, Pe is a maximum at the infusion point and decreases with distance from the infusion point. In the limit of infinitely large Pe, convection dominates fluid transport everywhere and diffusion can be neglected, which yields the convection-dominated penetration distance $R_c$ as a function of time T $$R_C = (3QT/4\pi\phi)^{1/3} \quad (12)$$

This model is well suited for infusions into gels where there are no elimination mechanisms.

Results

Device Characterization

Constant pressure infusions were controlled by a pressure injector, which sets the pressure upstream of the microchannel to a desired value. However, there is a significant pressure loss over the length of the microchannel, which must be taken into account to find the infusion pressure, $P_o$, at the microchannel exit. To determine this pressure loss as a function of flow rate, flow rates in the microchannel were measured for several injector pressures with the exit of the microchannel outlet immersed in a water reservoir (0 ga pressure). A linear relationship between flow rate and injector pressure was found, which is expected because flow in the microchannel is laminar. The pressure drop $\Delta P$ between the injector and the microchannel exit was found to be $\Delta P$ (in kPa)=70.0 Q (in μL/min). Therefore, during an infusion experiment, Q was measured and this formula was used to find μP, which was then subtracted from the injector pressure to determine the pressure at the channel outlet, $P_o$.

Distributions of Infused Compounds and Backflow

Figure 13:
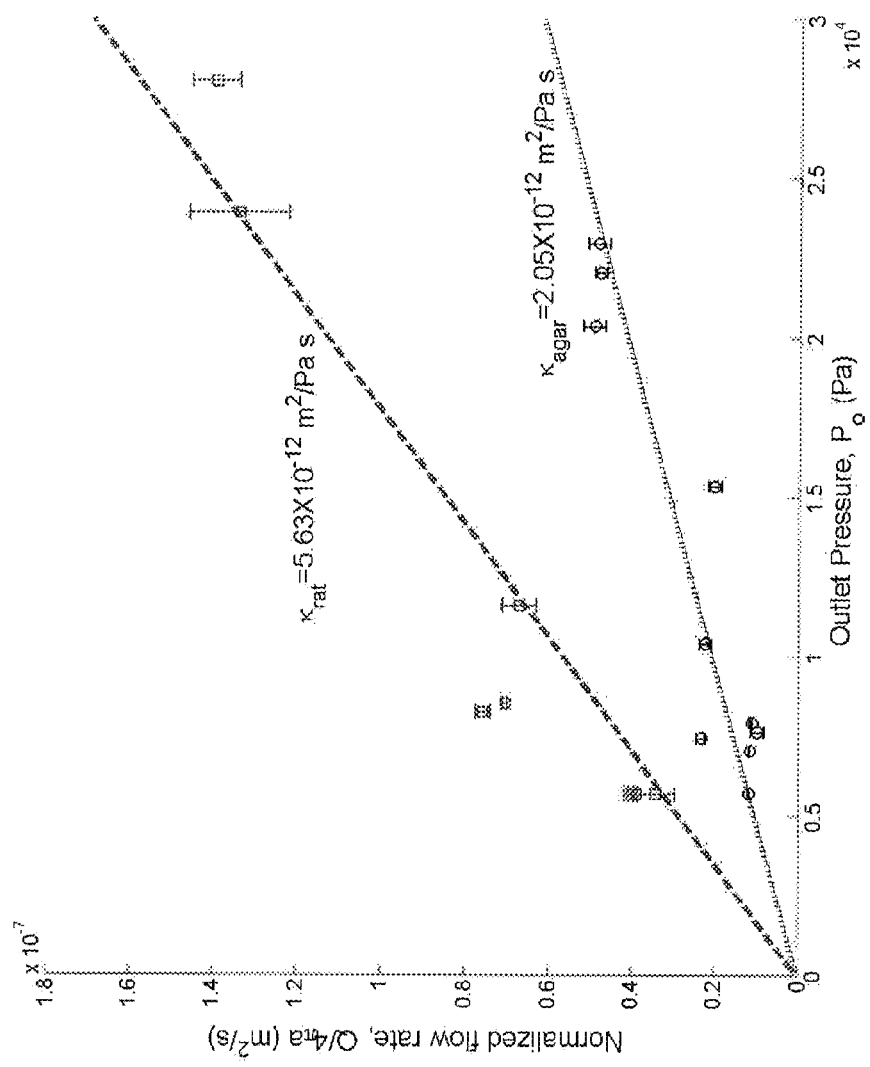
FIG. 13 shows a graph from which the apparent hydraulic permeability was calculated using Darcy's Law in radial coordinates, where $P_o=(Q(a)/4\pi a)\kappa$, for injection into 0.6% agarose (○) or brain (□); the x-axis is the pressure at the tip of the device; the injector pressure upstream from the device was 7-210 kPa; the flow rate was estimated by measuring the time it took for 1 μL of volume to be expelled through the device into the gel or tissue; each symbol represents one infusion; there were 5-20 measurements taken for each infusion depending on the infused volume and the error bars represent one standard deviation from these measurements; best fits of Eq. (8) to experimental data are shown by dashed lines.
Figure 14B:
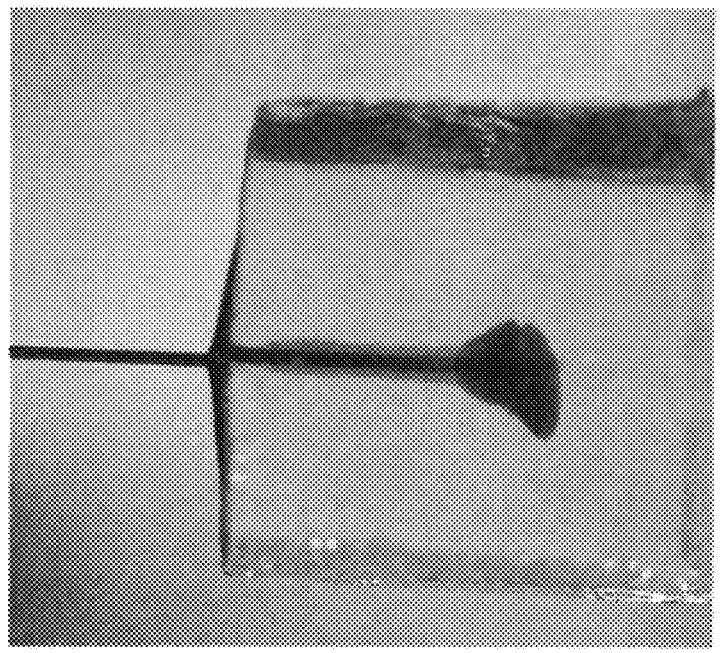
FIGS. 14A and 14B are comparative photographs showing dye diffusion from an exemplary CED device and from a 30 ga needle, respectively, according to an illustrative embodiment of the invention.
Figure 14A:
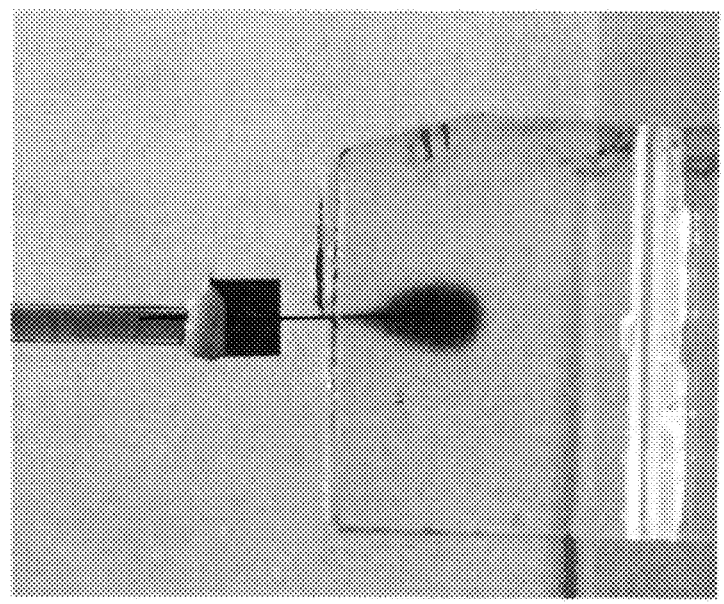

The infusion of dye into agarose gels was studied for injector pressures of 7, 35, 70, 140, 210, and 310 kPa, which corresponded to infusion flow rates of 0.08, 0.4, 0.8, 1.7, 2.9, 4.5 μL/min, respectively. In every case, the infusions resulted in spherically symmetric dye distributions about the exit of the microchannel. There was no visual evidence of backflow at any of these injector pressures. The graph in FIG. 13 shows a linear relationship between $Q(a)=4\pi a$ and $P_o$; according to Eq. (8), the slope of this line gives an apparent hydraulic conductivity for 0.6% agarose of $2.05 \times 10^{-12}$ m²/Pa s. Even at the lowest injector pressure (7 kPa), penetration of the dye was observed immediately, suggesting that the probe outlet was not occluded. There was no evidence of a pressure barrier to initiate flow. In contrast, for infusion through a blunt 30 ga needle inserted into the gel in the same manner, the pressure had to exceed 11 kPa before there was evidence of flow. To compare the performance of the microfabricated device with that of a needle, the injector pressure was increased in stages until the onset of backflow was observed. For the microfluidic device at an insertion depth of 5 mm, the backflow was observed when pressure was increased to 310±8 kPa (n=10) corresponding to a flow rate of 4.5 μL/min. For a 30 ga needle backflow was observed when the pressure was increased to 20 kPa±4 (n=10) corresponding to a flow rate of 0.41 μL/min (see, e.g., FIG. 14A, B showing the dye distribution for an exemplary CED microfluidic probe ($Q_{max}$=4.5 μL/min; $P_{critical}$=0 kPa) versus that for a 30 ga needle ($Q_{max}$=0.4 μL/min; $P_{critical}$=11 kPa), respectively).

Figure 15:
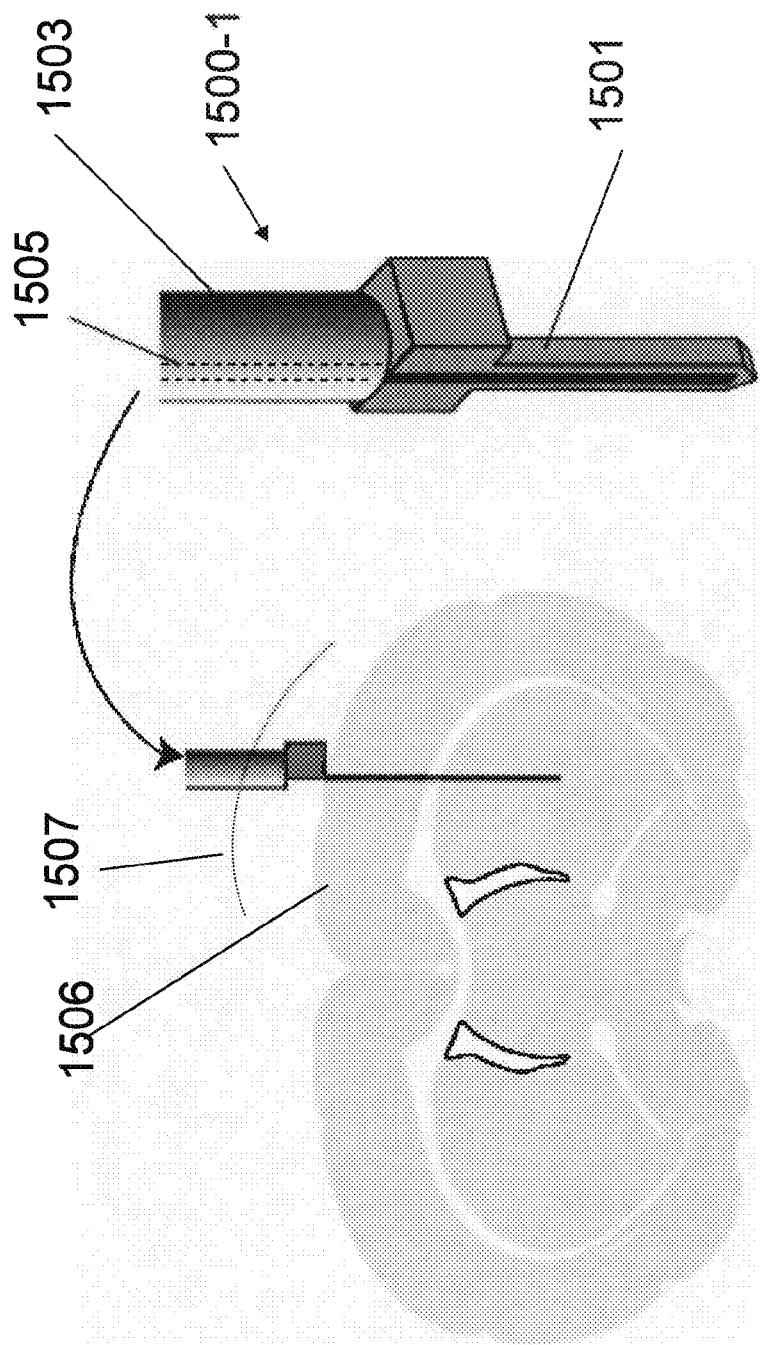
FIG. 15 is a schematic representation showing both a CED device with attached fluid reservoir inserted into a rat brain according to an illustrative embodiment of the invention as well as an extended CED device illustrating insertion into relatively thicker target tissue (e.g., human)
Figure 16:
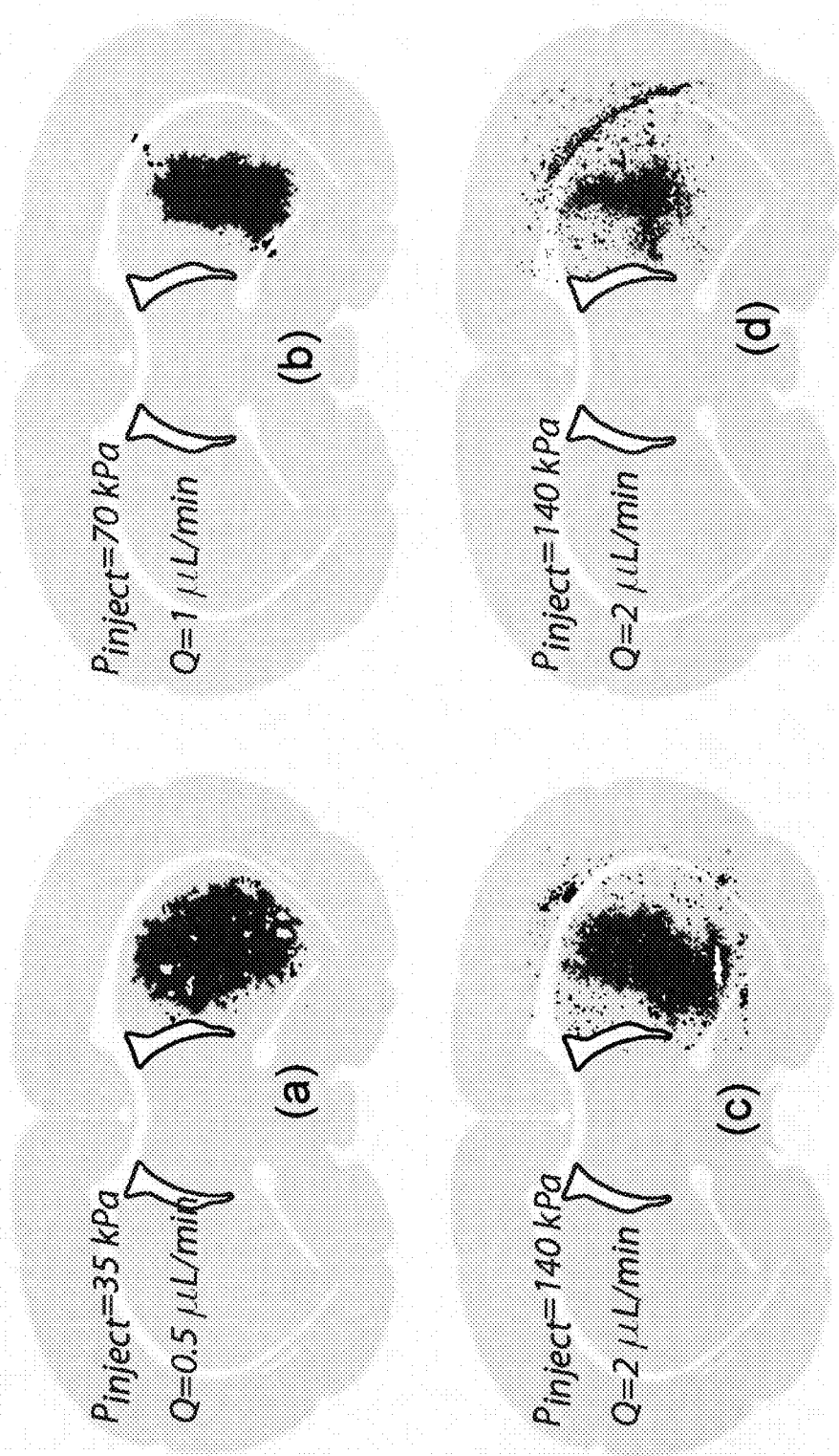
FIGS. 16(a-d) show overlays of processed data on a cartoon of the insertion site as in FIG. 15 to illustrates the pressure dependence of the dye distribution at different injection pressures according to an illustrative embodiment of the invention.

The device was inserted 3 mm laterally from bregma into the caudate of the rat to a depth of 5 mm as schematically illustrated, for example, in FIG. 15. The infusion of dye was studied for injector pressures of 35, 70, and 140 kPa as illustrated in FIGS. 16(a-d). In these cases the infusions resulted in dye distributions that were nearly elliptical except in one case at 140 kPa. FIG. 13 shows that the relationship between flow rate and pressure at the outlet of the channel, $P_o$, was linear, and a comparison of data with Eq. (8) yielded a value of $5.63 \times 10^{-12}$ m²/Pa s for the apparent hydraulic permeability of gray matter in the caudate putamen.

The shapes of the dye distributions in the rat brain depended on the injector pressure. At an injector pressure of 35 kPa, the distribution of dye within each coronal section was slightly non-spherical. At 70 and 140 kPa the distributions were more elongated. Single factor analysis of the variance (ANOVA) was performed on both the total volume of dye in the gray matter and the aspect ratio of the distribution at the infusion site (3 mm lateral from bregma). Tables 1 and 2 show a summary of the ANOVA results for an alpha value of 0.05 for volume and aspect ratio, respectively. In both cases there were statistically significant (p<0.05) differences between the low, medium, and high pressure groups. However, there was not a statistically significant difference in the aspect ratio beyond the infusion site. This result suggests that asymmetrical distribution was limited to tissue immediately adjacent to the device.

Evidence of backflow was found in one of three cases for an injection pressure of 140 kPa but in no cases for 35 or 70 kPa. In this case, the infused dye migrated into the white matter of the corpus callosum immediately above the caudate as a result of backflow along the outside of the microchannel. Once in the white matter, the dye then flowed in anterior and posterior directions. Backflow in this case may have been caused by a poor insertion, which can increase the likelihood of backflow. During curing of the epoxy, occasionally the device can become slightly misaligned with the micropipette that holds it. In this event the device is not exactly perpendicular to the surface as it is inserted, which can lead to tissue tearing and backflow.

Owing to the small size of the rat brain, dye reached white matter even in the absence of backflow. The caudate putamen is the largest area of homogeneous gray matter. It is roughly spherical with a diameter of approximately 3.0 mm and is surrounded by a white matter envelope consisting of the corpus callosum. Infused albumin reached the anterior forceps of the corpus callosum at a penetration distance of 2 mm and subsequently flowed several millimeters in the anterior direction. Such extensive penetration is unlikely in gray matter, but it could occur by transport through the high permeability tracts of white matter.

TABLE 1

Analysis for the variance of volume of dye in the gray matter between low (35 kPa), medium (70 kPa), and high (140 kPa) injector pressures

| Groups | Count | Sum | Average | Variance | |
|---|---|---|---|---|---|
| Low pressure | 3 | 7.6 | 2.5 | 0.11 | |
| Medium pressure | 3 | 8.3 | 2.8 | 0.17 | |
| High pressure | 3 | 11.4 | 3.8 | 0.01 | |
| Source of variation | SS | df | MS | F | P-value | F crit |
| Between groups | 3.5 | 2 | 1.8 | 18 | 0.02 | 9.6 |
| Within groups | 0.3 | 6 | 0.10 | | | |
| Total | 3.8 | 8 | | | | |

TABLE 2

Analysis for the variance of the aspect ratio at 0 mm from bregma between low (35 kPa), medium (70 kPa), and high (140 kPa) injector pressures

| Groups | Count | Sum | Average | Variance | |
|---|---|---|---|---|---|
| Low pressure | 3 | 3.6 | 1.2 | 0.004 | |
| Medium pressure | 3 | 4.91 | 1.6 | 0.068 | |
| High pressure | 3 | 4 | 1.3 | 0.002 | |
| Source of variation | SS | df | MS | F | P-value | F crit |
| Between groups | 0.32 | 2 | 0.16 | 6.4 | 0.03 | 5.1 |
| Within groups | 0.15 | 6 | 0.025 | | | |
| Total | 0.47 | 8 | | | | | the Effect of Diffusion on Penetration Distance

The potential advantage of CED is that penetration into tissue can be enhanced by convection compared with the penetration obtained by diffusion in controlled release. Convection dominates diffusion near the microchannel tip, but the infusion velocity decays as $1/r^2$ where r is the distance from the tip. If the infused drug penetrates sufficiently far from the infusion point, then its transport may be dominated by diffusion at its farthest penetration. The distance where this occurs depends not only on the infusion rate but also on the diffusivity of the injected molecules.

Figure 17:
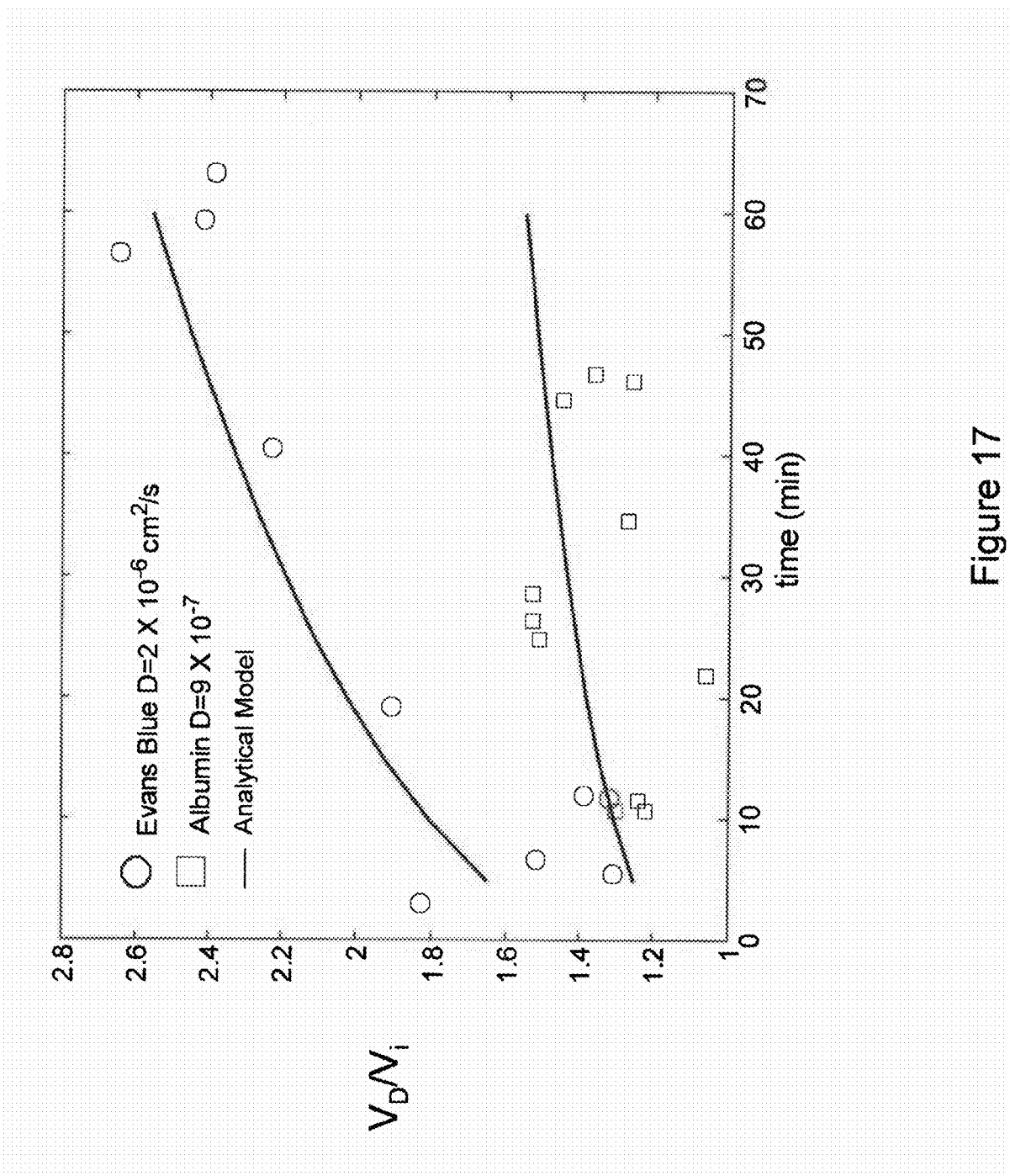
FIG. 17 is a graph showing volume distributed: volume infused of Evans Blue (○) and albumin (□) into 0.6% agarose at an infusion pressure of 5 kPa and a comparison to model predictions (–); each data point represents a separate infusion; the model accurately predicts the time dependent $V_d$:$V_i$ observed with infusion of Evans Blue ($R^2$=0.70) compared to the relatively time insensitive results obtained during infusion of albumin ($R^2$=0.83) according to an illustrative embodiment of the invention.

To show how diffusion can affect the penetration distance in CED, infusions into agarose were compared for two infused molecules: a small water soluble molecule (Evans Blue) and a large globular protein (albumin). Infusions of various durations were performed and the volume of gel containing dye $V_d$ was measured and compared with the known volume of fluid $V_i$ that was infused. FIG. 17 shows the ratio $V_d/V_i$ as a function of infusion time. In the absence of diffusion, corresponding to an infinitely large Peclet number everywhere throughout the flow, the ratio $V_d/V_i$ would equal the inverse of the porosity $1/\phi$ regardless of the infusion time. However, the data show that the ratio depends on infusion time, which indicates that diffusion affects the penetration distance. The ratio is larger and shows greater sensitivity to infusion time for Evans Blue, which is expected from Eq. (11) based on its larger diffusivity ($D=2.0\times10^{-6}$ cm$^2$/s, Stokes-Einstein equation, molecular radius from Markou et al., *A novel method for efficient drug delivery*, Ann. Biomed. Eng., 26 (1998) 502-511) compared with the diffusivity of albumin ($D=8.3\times10^{-7}$ cm$^2$/s in 0.3% agarose). Data for both compounds were compared with the model described above by using Eq. (11) to estimate the penetration depth for the appropriate experimental parameters. The result shown in FIG. 17 shows good agreement between the model and the data over a wide range of infusion times. The coefficient of multiple determination ($R^2$) was 0.70 for Evans Blue and 0.83 for albumin.

Discussion

The microfabricated devices described here have several advantages over larger needles for CED. The devices can deliver liquids at flow rates comparable to those in CED with needles with reduced backflow that often hampers fluid delivery through needles. Devices can be fabricated for specific anatomical geometries with the option of placing several delivery outlets on a single device. In addition, other components can be incorporated into microfabricated devices, including recording/stimulating electrodes, pumps, valves, and flow meters.

Infusing at constant pressure rather than at constant flow rate has important consequences on the pressure and stress distributions in the tissue. For constant pressure infusion, the pressure profile in the tissue is independent of the tissue's material properties (Eq. (6)), including its hydraulic permeability. Furthermore, it has been shown that for constant pressure infusion into a poroviscoelastic material, the radial and circumferential stress components also are independent of the hydraulic permeability. In contrast, the pressure and stress components are strongly affected by the hydraulic permeability for constant flow rate infusion. If sufficiently high levels of stress incite apoptotic or necrotic signaling cascades in neurons or glial cells, then knowing the stress profile even when the hydraulic permeability is uncertain is an advantage of constant pressure infusion.

There is a wide range of values reported for hydraulic permeability in tissues and gels (from $1\times10^{-11}$ to $1\times10^{-16}$ m$^2$/Pa s). Our value of $2.05\times10^{-12}$ m$^2$/Pa s for gray matter in the rat agrees reasonably well with a published estimate of $5\times10^{-12}$ m$^2$/Pa s. However, the permeability of elastic or viscoelastic porous media depends on deformation of the media. For example, it has been shown that the permeability of agarose decreases in uniaxial flow owing to compression of the void space in the gel. In a radial source flow like the one presented here, the magnitudes and signs of the radial and circumferential stress components determine whether the tissue is dominated by compression or tension. One group of investigators found an increase in permeability with respect to infusion pressure in radial flow in fibrosarcomas under constant pressure infusion (2-16 kPa) of albumin. For constant pressure infusion with our microfluidic probes, the apparent hydraulic permeability did not depend on flow rate in agarose or in brain tissue. However, the apparent hydraulic permeability is calculated based on the pressure and flow rate at one point, the infusion site. To distinguish local permeability changes in response to flow, it would be advantageous to measure pressure as a function of distance. The apparent value we report may overestimate the actual permeability of a poroelastic medium since dilation is expected to be greatest at the infusion site, leading to increased porosity and higher permeability there.

Several investigators have observed an increase in pressure followed by a precipitous decrease to a steady-state value at the beginning of constant flow rate infusions. This result has been attributed to the elasticity of brain tissue, the opening of fluid channels in the extracellular matrix, and simply occlusion of the needle tip. Our observations are consistent with the last explanation. During constant pressure infusion into 0.6% agarose using a blunt needle we found that a critical pressure (~10 kPa) was necessary to observe convective flow. When the pressure was increased to values only slightly larger than this critical pressure, a burst of dye was suddenly infused followed by significant backflow at insertion depths of 5 mm. The microfluidic devices did not exhibit any pressure increases during infusion. Infusion is observed immediately at the start, regardless of injector pressure.

The size of the delivery device for CED affects the maximum allowable infusion rate without backflow for a given insertion depth. A previous study of infusions of 4 µL of albumin through a 32 ga needle (OD=0.228 mm) into the caudate of rats showed that the maximum flow rate without backflow into the corpus callosum was 0.5 µL/min. Our exemplary microfluidic probes achieved flow rates of 2.0 µL/min (140 kPa injector pressure). In one animal, we found a crescent shape distribution (see FIG. 16) indicative of backflow into the corpus callosum. However, backflow in this case was most likely due to a poor insertion.

Using scaling arguments, Morrison et al., *Focal delivery during direct infusion to brain: role of flow rate, catheter diameter, and tissue mechanics*, Am. J. Physiol. Regul. Integr. Comp. Physiol. 277 (4) (1999) R1218-R1229, found $x_m$=constant $Q^{0.6} r_c^{0.8}$, where $x_m$ is the axial length of backflow, Q is the flow rate, $r_c$ is the catheter radius, and the constant is related to the physical properties of the porous medium. For infusions into the gray matter of rats they found $x_m$(cm)=11.41Q (µL/min)$^{0.6} r_c$(cm)$^{0.8}$ ($r_c^2$=area/(perimeter/2)). Applying this formula to the microfluidic probes using a hydraulic radius of 0.05 mm gives a maximum flow rate of 1.6 µL/min, which is similar to the observations presented herein.

Human clinical trials for the treatment of malignant gliomas with off-the-shelf catheters have shown promise in treating tumors and resection cavities. The large size of the targeted tumors (~1-5 cm) and kinetics of the cytotoxic agents require long infusion times (2-4 days) and high flow rates (5-10 µL/min). Applying Morrison's scaling relationship for gray matter to these high flow rates with a 32 ga needle gives backflow distances of one to 2 cm. A microfluidic device could be designed using the exemplary process described herein to have a hydraulic radius as small as 10 µm. If the scalings hold down to this size, such a device would result in backflow distances of only a few millimeters even at flow rates up to 10 µL/min.

The exemplary microfluidic CED devices are capable of delivering liquids at relevant flow rates for convection enhanced drug delivery. The small size and geometry of these devices offer potential advantages over traditional needle/catheter infusion protocols. The exemplary orientation of the channel inlets on the top of the device inhibits channel occlusion during insertion into tissue. The use of a small channel operating under constant pressure infusion leads to stress fields that are local (~100 µm) and independent of hydraulic permeability, which helps minimize backflow and produce spherical distributions of infused fluids, at least in porous media. Fluid distribution into the caudate of rats showed slight asymmetry. In direct comparison with needles in agarose brain phantoms, microfluidic devices could operate at ten times the flow rate before inducing backflow out of the brain phantom at a 5 mm insertion depth. Similarly, in vivo infusions into the caudate of rats were tolerated at flow rates four times higher than those previously reported.

Another embodiment of the invention is directed to a method for enhancing penetration of a drug-containing nanoparticle into brain tissue. In this regard, we investigated two methods for enhancing nanoparticle penetration into the brain during convection-enhanced delivery (CED). The first method was pre-treatment of the targeted tissue by enzymatic degradation. The second method used co-infusion of nanoparticles with hyperosmolar concentrations of mannitol. A microfluidic probe (as described above) was fabricated with two independently controlled channels, which allowed for simultaneous or separate delivery of nanoparticles and treatment solutions. Infusions were performed in the striatum of the normal rat brain. Monodisperse polystyrene particles with a diameter of 54 nm were used as a model nanoparticle system. Nanoparticles were infused after 30 min or 24 hr digestion by hyaluronidase, which degrades hyaluronan, the primary structural component of the brain extracellular matrix. There was a 70% increase in nanoparticle distribution volume after a 24 hr digestion with hyaluronidase, but no measurable change after 30 min. In normal and enzymatically degraded tissue, nanoparticles were entrained in the perivascular space of large blood vessels resulting in irregular distributions. Co-infusion of nanoparticles with 25% mannitol resulted in a 133% increase in nanoparticle distribution volume. Furthermore, co-infusion of mannitol into normal and enzymatically degraded tissue attenuated the entrainment of nanoparticles in perivascular spaces. Our results suggest that both enzymatic digestion and hyperosmolar infusions can be used to enhance nanoparticle penetration with CED, but hyperosmolar infusion has advantages over enzymatic digestion in terms of simplicity as well as extent and pattern of nanoparticle spread.

Figure 23:
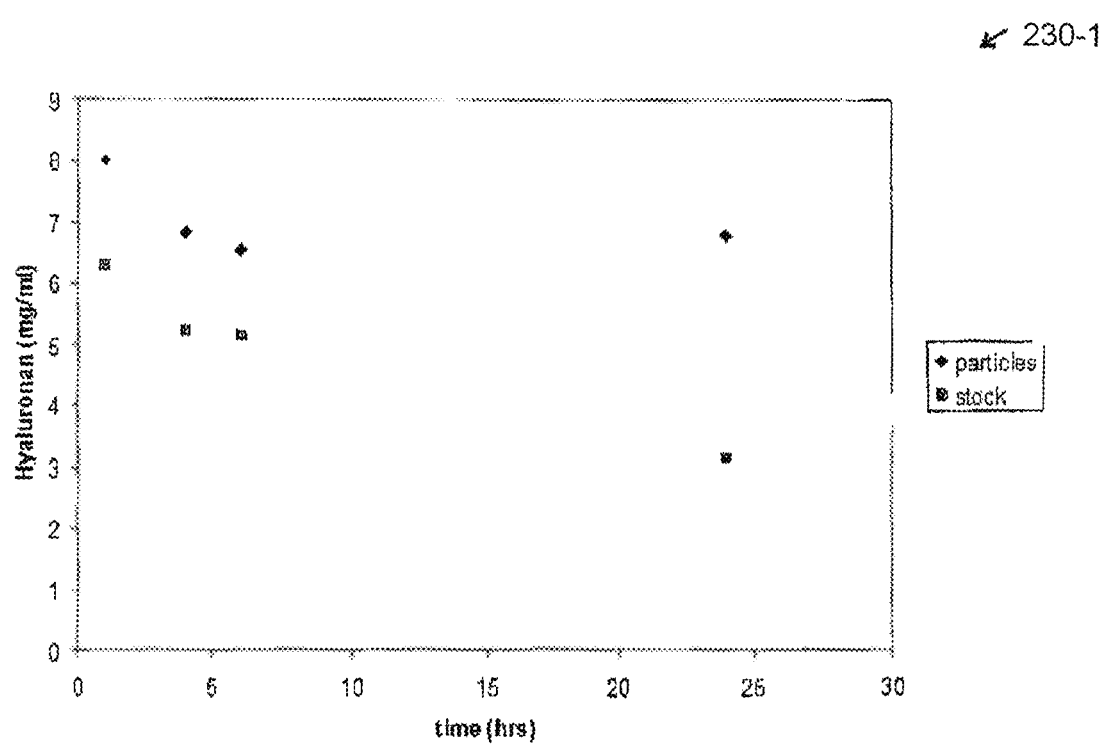
FIG. 23 is a graph that shows how the activity of nanoparticles containing immobilized enzyme tracked the activity of an enzyme-incubated stock solution.

Our studies did indicate that immobilizing an enzyme to the nanoparticles provided substantial enzyme activity after immobilization. Polystyrene nanoparticles wrer purchased with carboxcylic acid surfaces. Hyaluronidase was covalently attached to the surface of the nanoparticles using carbodiimide chemistry and a procedure similar to the one included with the nanoparticles. More particularly, the carboxcylic acid groups on the surface of the particles were activated by N-Ethyl-N?-(3 dimethylaminopropyl)carbodiimide (EDAC) in a buffered solution. Hyaluronidase was then added to the solution where the amine groups of the enzyme formed amide bonds with the carboxyl groups. To demonstrate enzymatic activity, we incubated a stock solution of hyaluronan with either hyaluronidase or nanoparticles coated with hyaluronidase. The amount of enzyme was chosen by estimating the amount added to the nanoparticles. We used a turbidimetric assay to determine hyaluronan concentration. The nanoparticles were 100 nm PS covalently modified with hyaluronidase, the same kind of enzyme used in the CED experiments described above. The graph 2301 in FIG. 23 shows that the kinetics look similar with the exception that the nanoparticle started to pellet overnight in the incubator; thus the 24 hour time point is somewhat less than expected.

Many promising treatments for brain diseases involve nanoparticles as drug or gene carriers. The blood-brain barrier prevents most particles from penetrating into the brain, making intracranial infusions, or convection-enhanced delivery (CED), an attractive drug delivery strategy. However, transport of particles through the extracellular space of tissues is hindered by the large size of nanoparticles (10-100 nm), which are much larger than small molecule drugs or therapeutic proteins that more easily penetrate the brain extracellular matrix (ECM). Results suggest that nanoparticles can penetrate brain tissue provided that particles are less than 100 nm in diameter, are neutral or negatively charged, and are not subject to rapid elimination mechanisms.

Studies have been conducted and reported of CED of liposomes in animal tumor models. Initial studies involving two sizes of liposomes showed that 40 nm liposomes distributed throughout the striatum of rats, but that 90 nm liposomes were confined to regions near the infusion point. Infusion of polystyrene particles showed similar effects of particle size. The distribution volume for 100 nm polystyrene particles was about half of that for 40 nm particles. The effective pore size of the extracellular matrix of gray matter has been estimated to be between 38 and 64 nm, which may explain why larger particles have difficulty moving through the ECM. Other factors also may limit the extent of particle penetration in the brain.

It is known that nanoparticles can be entrained in white matter and in necrotic zones of brain tumors; also, liposomes can accumulate in and move through perivascular spaces. Transport through perivascular spaces is thought to be an important part of fluid removal from the brain. It has been suggested that preferential transport through the perivascular space is responsible for some of the side-effects reported from CED and gene therapy clinical trials. It may be possible to increase the effective pore size and enhance the penetration of nanoparticles in tissue by selective enzymatic digestion of some ECM components. For example, investigators have reported a 100% increase in the diffusivity of IgG following collagenase treatment of xenografted tumors. Unlike most other tissues, the extracellular matrix of the brain has a low content of fibrous matrix proteins such as collagen. Brain ECM primarily consists of a family of proteoglycans called lecticans and the two components to which they bind, tenascins and hyaluronan (HA). These three macromolecules form a ternary structure in the extracellular space of the adult brain. HA serves as the structural backbone of the brain ECM, and highly charged chondroitin-sulphate proteoglycans (CSPG) side chains anchor the ECM to cells and blood vessels. HA and CSPG can be selectively degraded in the brain by hyaluronidase and chondroitinase, respectively. However, some hyaluronidases cleave glycosidic bonds in CSPGs as well as those in HA.

A second method to enhance nanoparticle penetration is to dilate the extracellular space. Infusion of a hyperosmolar solution into the extracellular space leads to a water flux out of surrounding blood vessels and cells, which increases the effective pore size of the ECM. For example, infusion of a hyperosmolar concentration of mannitol has been shown to enhance viral vector distribution and gene expression in bolus injections of AAV vectors in animal models for Alzheimer's disease and Sandhoff disease. Co-infusion of mannitol and liposomes has been shown to enhance penetration of liposomes into the striatum of rats.

In conjunction with the instant embodiment, a two-channel microfluidic probe was fabricated (as described above) to deliver two separate solutions at the same infusion site in the brain. The probe was used to deliver an enzyme solution through one channel and nanoparticles through the other channel. Isotonic and hyperosmolar solutions of particles were infused into normal and enzyme-treated brain. The enzymatic and hyperosmolar treatments both produced increases in the distribution volume of nanoparticles.

Microfluidic Probe Fabrication and Experimental Set-up

Figure 18:
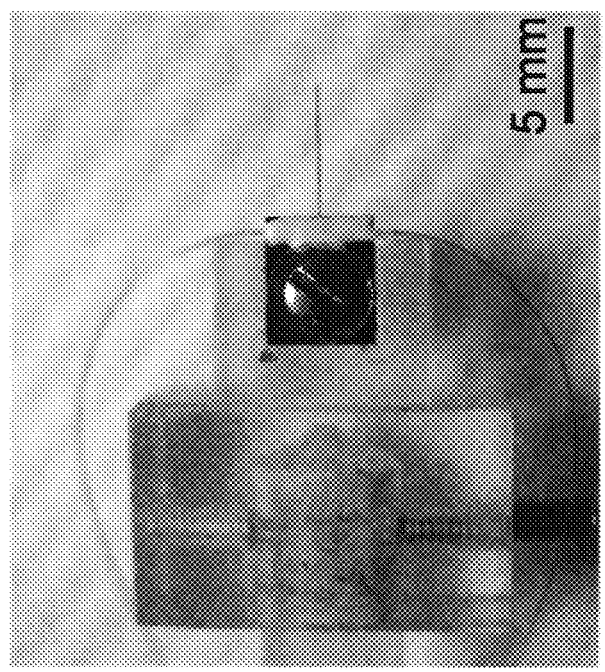
FIG. 18 is a photograph of an experimental dual channel CED device; each channel has its own protrusion for connection to small bore polyimide tubing; the device is fastened to a custom holder using a screw and washer, according to an exemplary embodiment of the invention.

An exemplary two-channel microfluidic probe (see, e.g., FIG. 8) was fabricated using standard micromachining methods as described above. Briefly, two parallel microfluidic channels were formed on a silicon substrate using a Parylene C structural layer (Specialty Coating Systems, Indianapolis, Ind.) and a sacrificial layer of photoresist (Shipley 1075, Phoenix, Ariz.). The cross-sectional area of each channel was 10×25 µm. The probe geometry was defined by front-side and back-side deep reactive ion etching of the silicon substrate. The exemplary probe had three main features; 1) a 6 mm long shank with a cross-sectional area of 100×100 µm for insertion into tissue, 2) a 5×5 mm base with a hole in the middle for fastening the device to a custom holder, and 3) two protrusions with cross-sectional areas of 70×100 µm for connecting the probe to polyimide tubing. FIG. 8 shows an electron micrograph of the probe and channels, while FIG. 18 shows a photograph of the actual probe attached to its holder.

The custom holder consisted of a 10×10×10 mm block of polycarbonate attached to a 6.4 mm diameter polycarbonate rod. The block contained a 5×5×0.5 mm milled recess. The probe was secured to the holder using a 0-80 stainless steel screw and a polycarbonate washer. Polyimide tubing (Small Parts Inc., Miami Lakes, Fla.) was glued over the silicon protrusions using two-part epoxy (Epoxy 907 Adhesive System, Miller-Stephenson). The other end of the polyimide tubing was attached to graduated micropipettes (not shown in figure). The microfluidic channel, tubing, and micropipettes were backfilled by applying a 10 psi vacuum at the micropipette and immersing the probe tip into a beaker of the solutions to be infused. Compressed high purity nitrogen was used as a pressure source. A pressure injector (World Precision Instruments PM8000, Sarasota, Fla.) maintained a constant pressure at the inlet of the channel. The flow rate through the devices was determined by measuring the speed of the liquid front in the micropipette.

Preparation of Nanoparticles

Carboxylate-modified monodisperse polystyrene nanoparticles (Molecular Probes, FluoSpheres) were used as a model system to determine the role of particle size on penetration. The carboxylate-modified surface provides a highly charged and relatively hydrophilic particle compared with bare polystyrene. Non-specific binding was reduced by incubating a 0.02% solids solution of nanoparticles in 1% bovine serum albumin (BSA) in phosphate buffered saline (PBS) for four hours at room temperature. Proteins readily absorb to the surface of the polystyrene particles via hydrophobic interactions. Particle size was determined by static light scattering and particle zeta potential by mobility between charged parallel plates (Brookhaven Instruments Corp., ZetaPlus). The results for size and zeta potential are reported as an average and standard error of ten measurements. For sizing, stock solutions of particles and BSA-coated particles were diluted to $10^{11}$ particles/mL. For brain infusions, nanoparticle solid concentration was held constant at 0.02% or about $10^{13}$ particles/mL.

In vivo Nanoparticle Infusions

Twenty-five male Sprague-Dawley rats (270-305 g) were used in our study. All procedures were done in accordance with the regulations of the Yale University Institutional Animal Care and Use Committee. Rats were anesthetized with ketamine (100 mg/kg)/xylyzine (10 mg/kg) solution via intraperitoneal injection. The head was shaved and disinfected with butadiene/alcohol/butadiene wipes. An incision was made and a 1.5 mm diameter hole was drilled in the skull 3 mm laterally from bregma in the left hemisphere. The probe was inserted to a depth of 5 mm at a rate of 1 mm/sec with the micromanipulator on a stereotactic frame. The tissue was allowed to equilibrate mechanically for 2 min. An upstream pressure of 7.5-15 psi was applied to produce flow rates of 0.75-1.0 µL/min. The infused volume was 5 µL. Pressures up to 30 psi were needed for the more viscous 25% mannitol solutions. Following infusion, probes were left in place for 2 min to allow any excess pressure to dissipate and prevent reflux up the insertion cavity.

Two treatments were considered to enhance nanoparticle penetration—enzymatic degradation and osmotically induced dilation. Enzymatic degradation of the ECM was performed by infusing 5 µL of 1000 U/mL hyaluronidase (from bovine testes, Sigma H3506) at 1 µL/min through one channel of the probe. Following 30 min. of digestion, nanoparticles were infused through the second channel at a flow rate of 0.75 µL/min. Osmotically induced dilation was performed by mixing nanoparticles in a 25% mannitol solution and infusing 5 µL at a flow rate of 0.75 µL/min through a single channel.

To examine the effect of digestion time on particle penetration, some experiments were run with a 24 hr interval between infusion of hyaluronidase and infusion of nanoparticles. In these cases, the probe was removed after enzyme infusion, and the animal was allowed to recover. After 24 hr, the probe was reinserted for nanoparticle infusion. To avoid possible reflux of particles through the enzyme infusion site, we used a separate site for nanoparticle infusion. The enzyme infusion site was 3 mm lateral and 0.5 mm anterior from bregma and the nanoparticle infusion site was 3 mm lateral and 0.5 mm posterior from bregma. Both infusions were performed at a depth of 5 mm. Both isotonic and hyperosmolar solutions were infused into the degraded tissue following 24 hr digestion.

Determination of Nanoparticle Distribution

The animals were immediately sacrificed by decapitation following probe removal, and the brains were removed and frozen on dry ice. The brains were sectioned into 50 µm slices on a cryostat from 1.0 mm anterior to 1.0 mm posterior from the infusion site (2 mm total). Nanoparticle distribution was captured on a fluorescent stereoscope (Zeiss Lumar V.12) using a CY3 filter. The exposure time was optimized for each brain to achieve maximum dynamic range at the infusion site without saturation of any pixels on a CCD camera. The same exposure time was used for all slices in each brain. The volume of distribution of the nanoparticles was calculated using a custom Matlab script which generated a binary image from the greyscale images and calculated the area of particle penetration. The threshold for the binary operation was 10% of the maximum fluorescent intensity, pixel values from 25-255 were included in calculating the penetration area of each slice. There was no detectable background fluorescence from the tissue. The penetration volume was calculated by summing the penetration area in each slice and multiplying by the slice thickness (50 µm). A student t-test was used to determine statistical significance of changes in the volume distribution between control infusions and the treatments.

Histochemical Assessment of Hyaluronan Degradation

Degradation of HA was determined by staining with hyaluronic acid binding protein (HABP) following 1 µL infusions of 1000 U/mL hyaluronidase into the striatum following the same surgical procedure outlined above. Following degradation times of 30 min, 6, 12, and 24 hr brains were harvested and post-fixed in 4% paraformaldehyde in PBS at 4° C. for 4 days. The tissue was cryo-protected in 30% sucrose for 3 days, frozen at −70° C., and sectioned into 50 µm slices. Tissue slices were immersed in biotinylated HABP (50 µg/µL, Calbiochem 385911) in PBS and left overnight on an orbital shaker. Slides were then immersed Alexa 555-Streptavidin conjugate (2 mg/mL, Invitrogen S21281) for two hours. Following several washing steps in PBS, stained slices were mounted with ProLong Gold Antifade media (Invitrogen P36930) and covered. Fluorescent images were captured using the same set-up described for nanoparticle imaging.

Results

Figure 19:
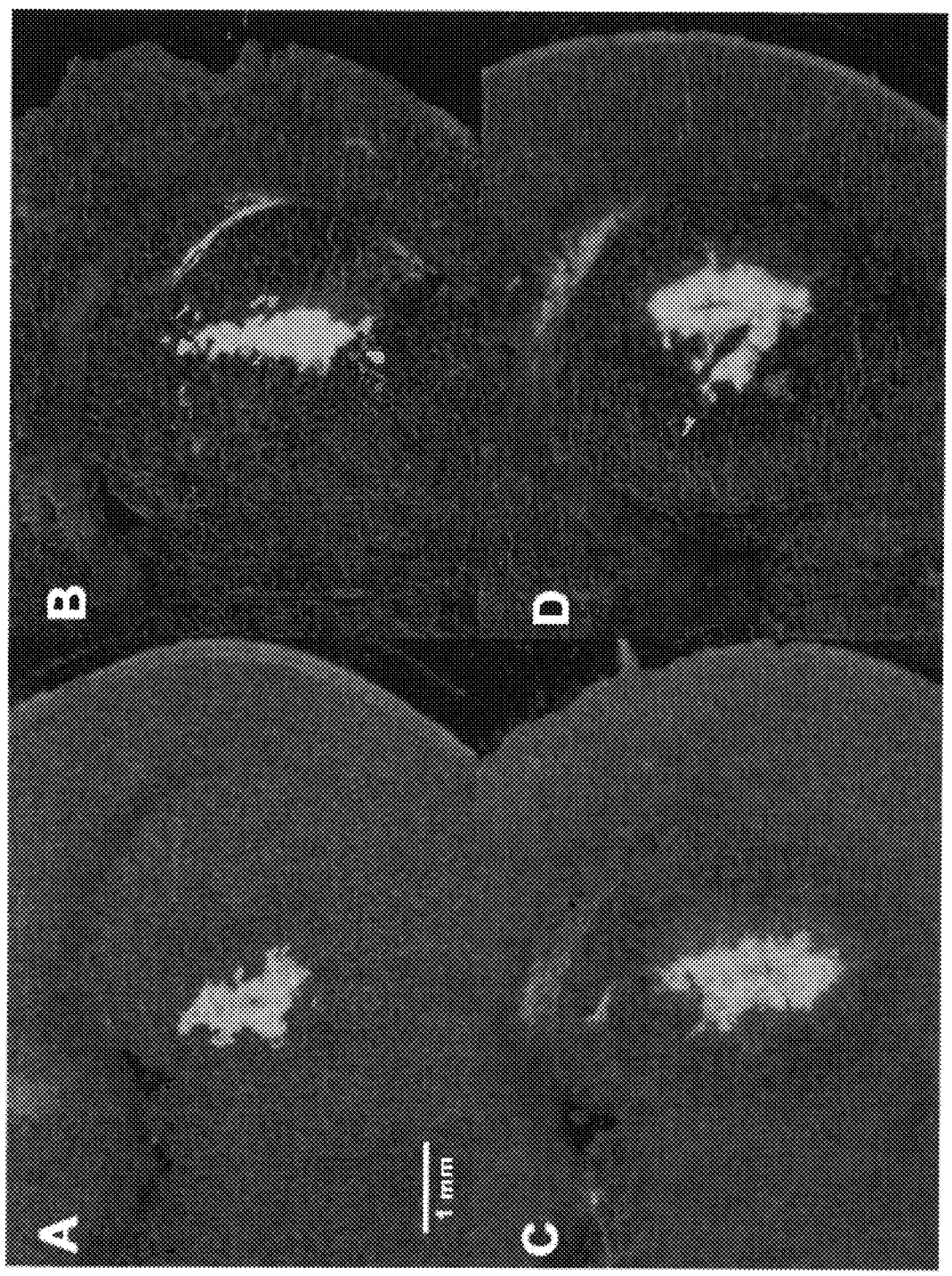
FIGS. 19(A-D) illustrate the distribution of nanoparticles shown as a merged image of fluorescent (pink-center) and bright field (blue-surrounding) images of tissue slices of a rat brain, according to an illustrative embodiment of the invention.

FIGS. 19(A-D) show typical distributions of fluorescent particles for the range of conditions studied: nanoparticle infusion with enzymatic pre-treatment, nanoparticle and mannitol co-infusion, and nanoparticle infusion without mannitol or enzymatic pre-treatment (the control). Table 3 shows the volume of nanoparticle distribution for each condition, which was determined by analysis of sets of these images.

TABLE 3

| Treatment | n | $V_d$ (mm$^3$) | range | p-value |
|---|---|---|---|---|
| Control | 4 | 1.00 ± 0.42 | 0.53-1.40 | — |
| Mannitol co-infusion | 3 | 2.33 ± 0.09 | 2.27-2.43 | 0.0034 |
| Hyaluronidase (24 hrs) | 3 | 1.70 ± 0.06 | 1.64-1.75 | 0.056 |
| Hyaluronidase (24 hrs) + Mannitol co-infusion | 3 | 2.09 ± 0.16 | 1.40-2.18 | 0.0069 |

There was an increase in distribution volume following a 24 hr digestion with hyaluronidase. However, no effect was measured for a 30 min digestion. Co-infusion of nanoparticles with mannitol into normal tissue showed the greatest increase in distribution volume. Mannitol co-infusion into enzyme-degraded tissue also increased distribution volume.

Nanoparticle Size and Charge

The measured diameter of the nanoparticles as received was 36.0±0.4 nm and the measured zeta potential was −33.4±2.2 mV. It is unknown whether the discrepancy between the supplier's quoted size (24 nm) and the measured size is due to aggregation or manufacturer error. To reduce aggregation, particle suspensions were sonicated in a water bath for 10 min and vortexed prior to sizing or infusion into animals. Incubation with BSA increased the diameter to 53.6±0.4 nm and decreased the zeta potential to −5.6±1.5 mV. The 18 nm increase in diameter is in good agreement with the reported hydrodynamic diameter of BSA (7.2 nm).

Enzymatic Degradation of the Extracellular Matrix

Initial studies showed that a 30 min. enzymatic digestion by hyaluronidase had no measurable effect on the nanoparticle distribution volume (data not shown). Therefore, we increased the digestion time to 24 hr based on previous reports of complete digestion of HA after 24 hr. After 24 hr, the distribution volume of nanoparticles in enzymatically degraded tissue was 70% larger than the distribution volume in normal tissue (Table 3). We assume that the hyaluronidase (55 kDa) penetrates through the entire striatum at an infusion volume of 5 µl because BSA (69 kDa), a similar sized protein, was able to penetrate throughout the striatum for similar infusion volumes at the same infusion site.

Figure 20:
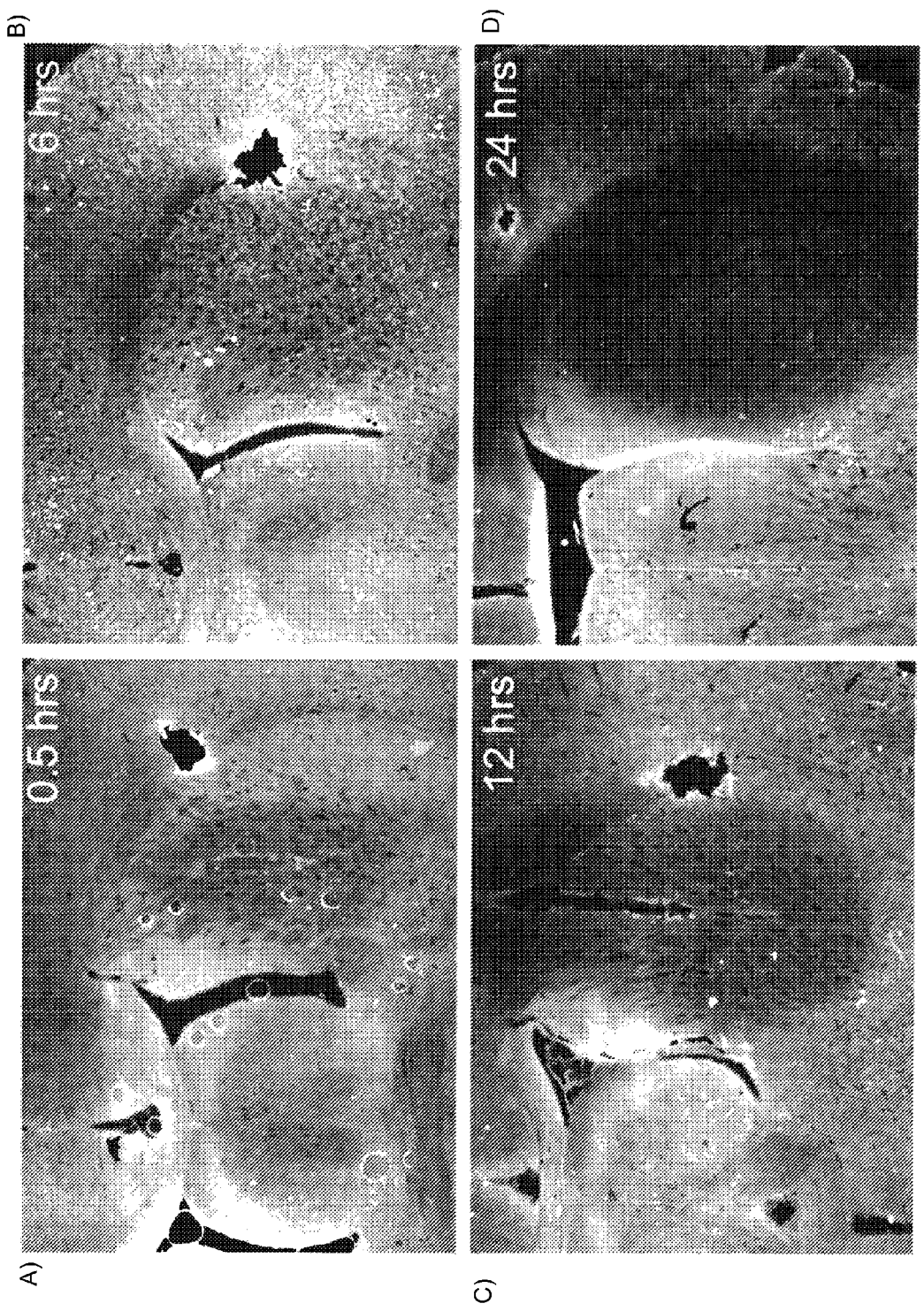
FIGS. 20(A-D) illustrate the degree of degradation of rat brain tissue by hyaluronidase at 30 min, 6 hr, 12 hr, and 24 hr after injection according to an illustrative embodiment of the invention.

The observation that nanoparticle penetration was enhanced at 24 hr of HA digestion was supported by histochemical staining for HA. FIGS. 20(a-d) show some evidence of degradation at 30 min (FIGS. 20a) and 6 hr (FIG. 20b) digestion times, but traces of HA were still evident near the infusion site, whereas, in tissue digested for 12 hr (FIGS. 20c) and 24 hr (FIG. 20d) there was widespread degradation of HA. The 24 hr incubation showed the most complete digestion of HA. Slices that were ±1 mm from the infusion site showed similar degradation of HA at 12 and 24 hr as shown in FIG. 18, while degradation was limited to a few hundred micrometers at 30 min and 6 hr. The deeper penetration of the hyaluronidase at longer digestion times was likely a function of both the kinetics of HA degradation and the diffusion of the initial 1 µl bolus.

Figure 21:
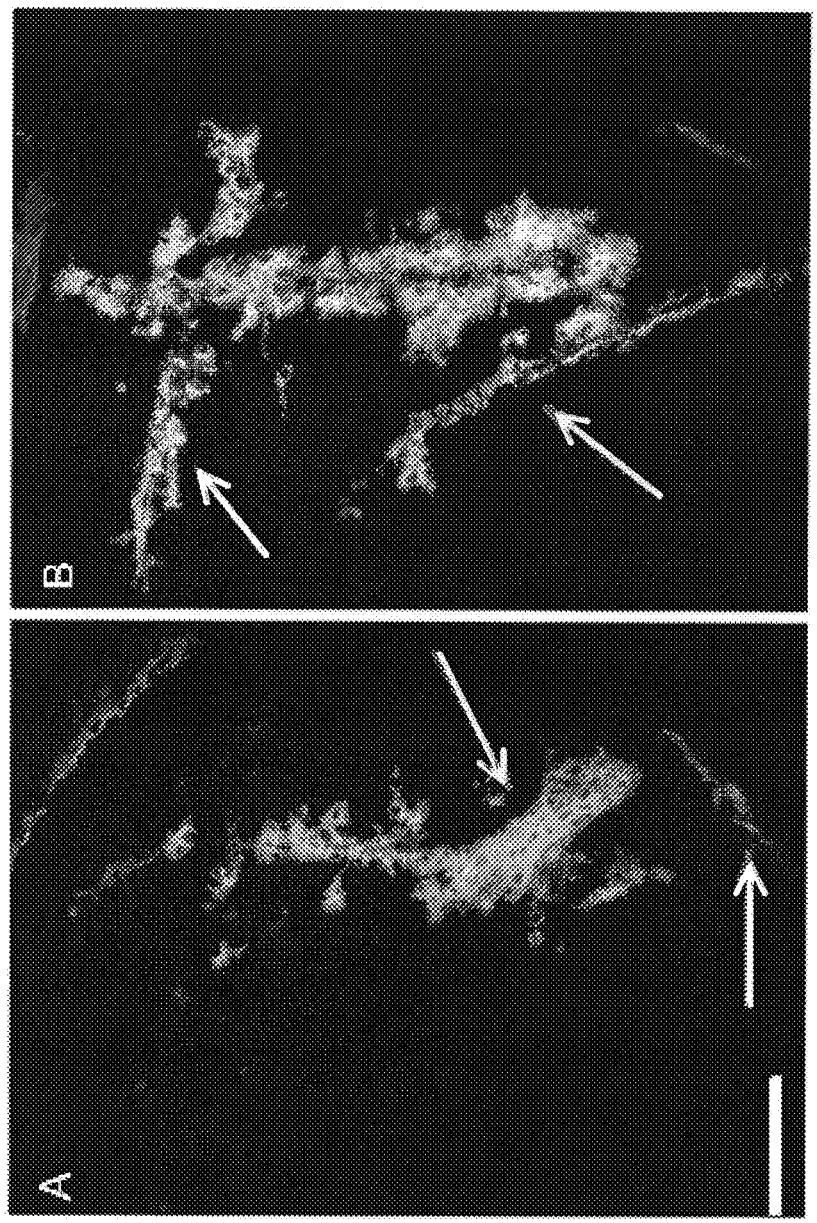
FIGS. 21A and 21B illustrates how nanoparticles were entrained within the perivascular spaces of cerebral arteries for infusions into both normal (A) and enzymatically degraded brain tissue (B); arrows point to arteries which significantly perturbed the distribution of nanoparticles; scale bar represents 1 mm, according to an illustrative embodiment of the invention.
Figure 22:
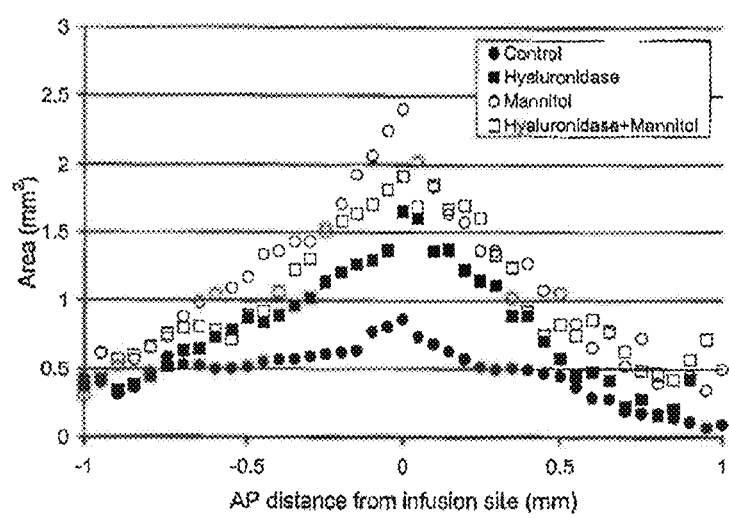
FIG. 22 is a graph that shows the area of nanoparticle distribution as function of distance from the infusion site according to an illustrative embodiment of the invention.

Nanoparticles were entrained in the perivascular space of large arteries both in normal and in enzyme-degraded tissue, as shown in FIGS. 21(A, B). The space between the vessel wall and the ECM forms a potential preferential path for nanoparticle transport, the branched pattern of perivascular spaces is similar to the pattern observed in FIG. 20. FIG. 22 shows the area of nanoparticle distribution as function of distance from the infusion site: for the enzyme treated tissue, the area of nanoparticle distribution is larger in slices close to the infusion point compared to untreated tissue suggesting that the tissue has less resistance to convection in the region nearest the source. It is possible that the degradation of hyaluronidase made the ECM less rigid locally and, thus, more susceptible to dilation during infusion. Since the pressure in the interstitium due to the infusion decreases inversely with distance from the infusion site, dilation maybe limited to tissue immediately adjacent to the infusion site.

Osmotic Dilation of the Extracellular Matrix

Dilation was induced by co-infusion of 25% mannitol with nanoparticles in untreated and enzyme-treated tissue. There was a significant increase in the distribution volume in both cases during mannitol co-infusion (Table 3). The greatest increase in distribution volume in all treatments occurred with mannitol co-infusion into untreated tissue. The increase in distribution volume was 23% between enzyme-treated tissue and degraded tissue with mannitol co-infusion, compared to 133% for untreated tissue and untreated tissue with mannitol co-infusion.

The branched structure of nanoparticle distribution indicative of perivascular transport was not observed for co-infusions with mannitol. As in the case of enzyme pre-treatment, co-infusion of mannitol into untreated tissue showed a peak in distribution area near the infusion site (FIG. 22). There was also change in the volume of particles near the infusion site between enzyme-treated tissue and enzyme-treated tissue with a mannitol co-infusion. There was a difference ($p=0.04$) between the total distribution volume (Table 3) for enzyme-treated tissue, although the difference was not as pronounced as in normal tissue. The hyaluronidase treatment, especially near the infusion site, appears to have mitigated some of the effect of the hyperosmolar treatment.

Discussion

One of the needs emphasized by clinicians whom perform CED protocols is better delivery devices. Most delivery devices are modified catheters or small tubing with a single end-port. These devices often lead to reflux and unpredictable drug distributions. The amount of reflux, or backflow, decreases with the diameter of the device.

Another useful feature in a fluid delivery system would be the ability to infuse from multiple ports along the length of the device. Attempts to infuse out of catheters with multiple ports usually results in flow from only the most proximal port. Here, we have demonstrated the ability to infuse solutions separately and independently through two channels. This microfluidic platform can be easily extended to include several independently controlled channels with outlets along the length of the device. Such devices could enhance the efficacy of CED protocols by allowing clinicians to turn multiple channels on/off in response to drug distribution as determined by real-time imaging techniques. In addition, multichannel devices allow for previously unavailable protocols that involve pretreatment and co-infusion strategies to improve drug distribution.

The effective pore size of normal gray matter has been reported to be between 38-64 nm, which would seem to preclude transport of many nanoparticles used for drug delivery. Yet there are reports of viral vectors and liposomes penetrating several millimeters in animal models, albeit in branched distributions. Some researchers have proposed that the perivascular space acts as a conduit for removing excess fluid and as a preferential pathway for nanoparticles. The branched nanoparticle distributions observed here for normal and enzyme-treated tissue are consistent with perivascular-dominated transport.

In our study we attempted to degrade HA, which resulted in a 70% increase in distribution volume of nanoparticles in normal brain tissue. Similar enzymatic treatments in tumors have shown similar effects on the diffusion and convection of macromolecules. For example, collagenase treatments greatly enhanced penetration of IgG by convection into ovarian carcinomas, although hyaluronidase treatments had no effect in that case. An alternative approach to pretreating tissues with enzymes is to immobilize enzymes to the surface of nanoparticles. Collagenase linked to superparamagnetic nanoparticles migrated through collagen gels at speeds of up to 90 $\mu$m/hr under the influence of a magnetic field. Our preliminary results with hyaluronidase immobilization to nanoparticles suggest that the lifetime of the enzyme can be extended by this approach.

HA and the structures it forms with other ECM components dictate intercellular transport in the normal brain. The degradation of HA produces mostly tetraoligosaccharides and hexaoligosaccharides that are incapable of chain-chain associations. These associations have been shown to hinder diffusion: they also likely hinder convection in untreated tissue, which could explain, at least in part, the increase in nanoparticle transport with hyaluronidase pre-treatment. However, HA also affects the mechanical response to infusion pressure within brain tissue. Complete degradation of HA after 24 hr would likely decrease the elastic modulus of brain tissue substantially, which could produce an increase in permeability and an enhancement of nanoparticle transport.

We also observed that mannitol co-infusion was less effective in increasing nanoparticle transport in enzyme-treated tissue than in untreated tissue. The aggregates formed between HA and CSPGs bind large amounts of water. If these aggregates are degraded by enzymatic treatment, then the remaining ECM may be less capable of absorbing additional water, which would be expected to diminish the effectiveness of hyperosmolarity induced by mannitol.

The 24 hr digestion time reported in our study could be unreasonable in a clinical setting since it would require multiple surgeries. Increasing the enzyme concentration may decrease digestion times, but the kinetics of hyaluronidase depend nonlinearly on HA concentration, which makes it difficult to predict whether a higher concentration would actually yield faster degradation. In our study, the hyaluronidase concentration and digestion time were not optimized; further work may well reveal that shorter exposures or alternate delivery techniques provide the same level of enhancement in transport. In addition, the infusion of alternate enzymes, including chondroitinases that specifically target CSPGs, may also lead to accelerated ECM digestion.

The clinical and biological consequences of degrading the brain ECM in humans are unknown. However, the ECM has been reported to return to normal twelve days after complete degradation of HA in the rat cerebrum. A possible complication of enzymatic degradation of tumors is promoting metastasis of tumor cells. Gliomas are known to migrate by expressing proteinases that degrade native ECM components and infiltrate healthy tissue. However, systemically administered hyaluronidase has improved the outcome of standard chemotherapy and boron neutron capture therapy for glioblastomas.

Hydraulic remodeling via co-infusion of hyperosmolar mannitol was more effective than enzymatic treatments for enhancing the penetration of nanoparticles in normal tissue. Others have reported a 50% increase in the distribution volume of 40 nm liposomes in the rat brain, while we observed a 133% increase for 54 nm polystyrene particles. However, the distribution volume was unchanged for 2 kDa dextran when it was co-infused with 20% mannitol, which suggests that hyperosmolar treatment may only enhance the penetration of particles that are sterically excluded from the ECM. In addition, transport through perivascular spaces was attenuated with mannitol treatments, perhaps due to the high viscosity of 20% mannitol. Others have reported that infusion of viral vectors into tumors in a viscous polymer solution blocked convection through microvessels. The simplicity and short response time to mannitol may make it a more attractive strategy than enzymatic degradation. The permeability effect of hyperosmolar treatments on the blood-brain barrier are reversed within 10 min and virtually no side-effects have been reported for treating edema with systemic administration of mannitol.

In conclusion, we have examined the penetration of nanoparticles in brain after controlled infusion with a novel microfluidic probe. The small size of the probe provides for improved delivery of clinically-relevant fluid flows into the brain; the presence of multiple channels offers the potential for treatment protocols that are unattainable by other means. We demonstrated the use of this microfluidic system for the combined infusion of nanoparticles and agents that potentially enhance nanoparticle transport through the ECM of brain. Our results suggest that both enzymatic treatments and exposure to hyperosmolar solutions significantly enhance the transport of polymer nanoparticles.

The foregoing description of the embodiments of the invention have been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A method of delivering a drug to a patient via convection-enhanced delivery, comprising:
providing an implantable convection-enhanced-delivery (CED) device, comprising:
a body having a shank portion at a distal end thereof and a fluid inlet portion that is contiguous with the shank portion;
at least one enclosed channel disposed in at least a portion of a length of the body, wherein the at least one enclosed channel has an inlet port adjacent a proximal end thereof that is adjacent a proximal end of the fluid inlet portion of the body and a distal end disposed in the shank portion,
further wherein the at least one enclosed channel has at least one outlet port along a length of the shank portion;
inserting the device into brain tissue of the patient to form a pathway in the brain tissue;
delivering a fluid containing a first drug under positive pressure through one of said at least one enclosed channel of the device into the brain tissue.

2. The method of claim 1, wherein delivering the fluid comprises infusing the fluid at a flow rate of 0.1 to 5.0 uL/min.

3. The method of claim 1, wherein delivering the fluid comprises infusing the fluid into the extracellular matrix of the brain.

4. The method of claim 1, wherein delivering the fluid comprises infusing the fluid at a constant pressure.

5. The method of claim 1, wherein the drug comprises AAV vector.

6. The method of claim 1, further comprising delivering a fluid containing a second drug under positive pressure through a second channel of the device into the brain tissue.

7. The method of claim 6, wherein the fluid containing the first drug and the fluid containing the second drug are delivered simultaneously.

8. The method of claim 6, wherein the fluid containing the first drug and the fluid containing the second drug are delivered sequentially.

9. The method of claim 6, wherein the second drug comprises a hyperosmolar solution.

10. The method of claim 9, wherein the hyperosmolar solution comprises a mannitol solution.

11. The method of claim 6, wherein the second drug comprises an enzyme configured to digest an extracellular matrix of the brain.

12. The method of claim 11, wherein the enzyme comprises hyaluronidase.

* * * * *

UNITED STATES PATENT AND TRADEMARK OFFICE
CERTIFICATE OF CORRECTION

PATENT NO. : 9,844,585 B2
APPLICATION NO. : 14/314119
DATED : December 19, 2017
INVENTOR(S) : William L. Olbricht et al.

It is certified that error appears in the above-identified patent and that said Letters Patent is hereby corrected as shown below:

In the Specification

Column 1, after the Federally Sponsored Research heading, delete the existing paragraph (Lines 17 - 26) and insert the following:
--This invention was made with government support under Grant Number NS045236 awarded by the National Institutes of Health and Grant Number ECS 0335765 awarded by the National Science Foundation. The Government has certain rights in the invention.--

Signed and Sealed this
Tenth Day of July, 2018

Andrei Iancu
*Director of the United States Patent and Trademark Office*